United States Patent
Dlugos et al.

(10) Patent No.: US 7,927,270 B2
(45) Date of Patent: Apr. 19, 2011

(54) EXTERNAL MECHANICAL PRESSURE SENSOR FOR GASTRIC BAND PRESSURE MEASUREMENTS

(75) Inventors: Daniel F. Dlugos, Middletown, OH (US); Amy L. Poeppelman, Mason, OH (US); David C. Yates, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1116 days.

(21) Appl. No.: 11/668,122

(22) Filed: Jan. 29, 2007

(65) Prior Publication Data

US 2008/0015406 A1  Jan. 17, 2008

Related U.S. Application Data

(63) Continuation-in-part of application No. 11/369,389, filed on Mar. 7, 2006, which is a continuation-in-part of application No. 11/065,410, filed on Feb. 24, 2005, now Pat. No. 7,699,770.

(51) Int. Cl.
*A61F 2/00* (2006.01)
(52) U.S. Cl. .......................... 600/37; 606/157
(58) Field of Classification Search ............... 600/29–32, 600/37, 593; 128/897–899; 604/27–28, 604/909; 607/41; 606/139–141, 151, 157, 606/201–203, 213, 228
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |

(Continued)

FOREIGN PATENT DOCUMENTS

AU  729 467  2/2001

(Continued)

OTHER PUBLICATIONS

European Search Report dated Jun. 19, 2009 for Application No. 09250581.

(Continued)

*Primary Examiner* — John P Lacyk
(74) *Attorney, Agent, or Firm* — Frost Brown Todd LLC

(57) ABSTRACT

A merely exemplary external pressure sensing system comprises a connecting member and a pressure sensor. The connecting member is operable to connect to a syringe barrel and a needle. The connecting member comprises a conduit permitting communication of fluid from the syringe barrel to the needle when the connecting member is connected to the syringe barrel and the needle. The pressure sensor is in communication with the conduit. The pressure sensor is configured to sense pressure of fluid within the connecting member. The connecting member is configured to permit the pressure sensor to sense the pressure of the fluid while the fluid is communicated from the barrel to the needle. The pressure sensor is configured to provide a visual indication of sensed pressure. The visual indication may be provided by a variety of components, including but not limited to a diaphragm, a disc, a needle, or a slider.

20 Claims, 17 Drawing Sheets

U.S. PATENT DOCUMENTS

| | | | |
|---|---|---|---|
| D25,318 S | 3/1896 | Perky | |
| D27,151 S | 6/1897 | Moulten | |
| D29,715 S | 11/1898 | Wheeler | |
| D29,745 S | 11/1898 | Bunker | |
| D29,885 S | 12/1898 | Gillespie et al. | |
| D30,690 S | 5/1899 | Schwedtmann | |
| D30,966 S | 6/1899 | Howe | |
| D31,230 S | 7/1899 | Hogan | |
| 689,758 A | 12/1901 | Shaw | |
| 724,913 A | 4/1903 | Montgomery | |
| 899,477 A | 9/1908 | Williams | |
| 926,197 A | 6/1909 | Kim | |
| 953,875 A | 4/1910 | Waring | |
| 991,192 A | 5/1911 | Battenfeld | |
| 1,087,988 A | 2/1914 | Sheldon | |
| 1,210,701 A | 1/1917 | Ryden | |
| 1,219,296 A | 3/1917 | Hahn | |
| 1,224,355 A | 5/1917 | Brown | |
| 1,263,914 A | 4/1918 | Martin | |
| 1,310,290 A | 7/1919 | Piechowicz | |
| 1,384,873 A | 7/1921 | Strickland | |
| 1,421,507 A | 7/1922 | Lindberg | |
| 1,551,525 A | 8/1925 | Hamer | |
| 1,560,973 A | 11/1925 | Cheron | |
| 1,620,633 A | 3/1927 | Colvin | |
| 1,623,403 A | 4/1927 | Friel | |
| 1,689,085 A | 10/1928 | Russell et al. | |
| 1,764,071 A | 6/1930 | Foulke | |
| 1,782,704 A | 11/1930 | Woodruff et al. | |
| 1,807,107 A | 5/1931 | Sternberch | |
| 1,865,446 A | 7/1932 | Sears | |
| 1,882,338 A | 10/1932 | Reed et al. | |
| 1,924,781 A | 8/1933 | Gaiser | |
| 2,027,875 A | 1/1936 | Odend'hal | |
| 2,063,430 A | 12/1936 | Graser | |
| 2,099,160 A | 11/1937 | Charch | |
| 2,105,127 A | 1/1938 | Petrone | |
| 2,106,192 A | 1/1938 | Saville | |
| 2,143,429 A | 1/1939 | Auble | |
| 2,166,603 A | 7/1939 | Menzer | |
| 2,168,427 A | 8/1939 | McConkey | |
| 2,174,525 A | 10/1939 | Padernal | |
| 2,178,463 A | 10/1939 | Bahnson | |
| 2,180,599 A | 11/1939 | Menasco | |
| 2,177,564 A | 12/1939 | Havill | |
| 2,203,460 A | 6/1940 | Fieber | |
| 2,206,038 A | 7/1940 | Ford | |
| 2,216,374 A | 10/1940 | Martin | |
| 2,223,699 A | 12/1940 | Norgren | |
| 2,225,145 A | 12/1940 | Baumbach | |
| 2,225,880 A | 12/1940 | Montelius | |
| 2,261,060 A | 10/1941 | Giesler | |
| 2,261,355 A | 11/1941 | Flynn | |
| 2,295,539 A | 9/1942 | Beach | |
| 2,303,108 A | 11/1942 | Blackburn | |
| 2,303,502 A | 12/1942 | Rous | |
| 2,318,819 A | 5/1943 | Verson | |
| 2,327,407 A | 8/1943 | Edyvean | |
| 2,327,615 A | 8/1943 | Ankarlo | |
| 2,354,571 A | 7/1944 | Blain | |
| 2,396,351 A | 3/1946 | Thompson | |
| 2,426,392 A | 8/1947 | Fennema | |
| 2,426,817 A | 9/1947 | Carlton et al. | |
| 2,440,260 A | 4/1948 | Gall | |
| 2,442,573 A | 6/1948 | Stafford | |
| 2,453,217 A | 11/1948 | Gregg et al. | |
| 2,455,859 A | 12/1948 | Foley | |
| 2,477,922 A | 8/1949 | Emery et al. | |
| 2,478,876 A | 8/1949 | Nelson | |
| 2,482,392 A | 9/1949 | Whitaker | |
| 2,494,881 A | 1/1950 | Kost | |
| 2,509,210 A | 5/1950 | Clark | |
| 2,509,673 A | 5/1950 | Church | |
| 2,511,765 A | 6/1950 | Bradbury | |
| 2,520,056 A | 8/1950 | Pozun | |
| 2,521,976 A | 9/1950 | Hays | |
| 2,533,924 A | 12/1950 | Foley | |
| 2,538,259 A | 1/1951 | Merriman | |
| 2,581,479 A | 1/1952 | Grashman | |
| 2,600,324 A | 6/1952 | Rappaport | |
| 2,606,003 A | 8/1952 | McNeill | |
| 2,615,940 A | 10/1952 | Williams | |
| 2,632,447 A | 3/1953 | Dobes | |
| 2,639,342 A | 5/1953 | Cope | |
| 2,640,119 A | 5/1953 | Bradford, Jr. | |
| 2,641,742 A | 6/1953 | Wolfe | |
| 2,651,304 A | 9/1953 | Browner | |
| 2,665,577 A | 1/1954 | Sanowskis | |
| 2,673,999 A | 4/1954 | Shey | |
| 2,676,609 A | 4/1954 | Pfarrer | |
| 2,684,118 A | 7/1954 | Osmun | |
| 2,689,611 A | 9/1954 | Martinson | |
| 2,697,435 A | 12/1954 | Ray | |
| 2,723,323 A | 11/1955 | Niemi | |
| 2,734,992 A | 2/1956 | Elliot et al. | |
| 2,740,007 A | 3/1956 | Amelang | |
| 2,740,853 A | 4/1956 | Hatman, Jr. | |
| 2,742,323 A | 4/1956 | Shey | |
| 2,747,332 A | 5/1956 | Morehouse | |
| 2,753,876 A | 7/1956 | Kurt | |
| 2,756,883 A | 7/1956 | Schreck | |
| 2,756,983 A | 7/1956 | Furcini | |
| 2,761,603 A | 9/1956 | Fairchild | |
| 2,773,312 A | 12/1956 | Peck | |
| 2,783,728 A | 3/1957 | Hoffmann | |
| 2,787,875 A | 4/1957 | Johnson | |
| 2,793,379 A | 5/1957 | Moore | |
| 2,795,460 A | 6/1957 | Bletcher | |
| 2,804,514 A | 8/1957 | Peters | |
| 2,822,113 A | 2/1958 | Joiner, Jr. | |
| 2,831,478 A | 4/1958 | Uddenberg et al. | |
| 2,864,393 A | 12/1958 | Drake | |
| 2,865,541 A | 12/1958 | Hicks | |
| 2,870,024 A | 1/1959 | Martin | |
| 2,883,995 A | 4/1959 | Bialous et al. | |
| 2,886,355 A | 5/1959 | Wurzel | |
| 2,895,215 A | 7/1959 | Neher et al. | |
| 2,899,493 A | 8/1959 | Levine | |
| 2,902,861 A | 9/1959 | Frost et al. | |
| 2,923,531 A | 2/1960 | Bauer et al. | |
| 2,924,263 A | 2/1960 | Landis | |
| 2,924,432 A | 2/1960 | Arps et al. | |
| 2,930,170 A | 3/1960 | Holsman et al. | |
| 2,938,592 A | 5/1960 | Charske et al. | |
| 2,941,338 A | 6/1960 | Santschi | |
| 2,943,682 A | 7/1960 | Ingram, Jr. et al. | |
| 2,958,781 A | 11/1960 | Marchal et al. | |
| 2,961,479 A | 11/1960 | Berting | |
| 2,976,355 A | 3/1961 | Levine | |
| 2,976,686 A | 3/1961 | Stelzer | |
| 2,977,876 A | 4/1961 | Meyers | |
| 2,986,715 A | 5/1961 | Church et al. | |
| 2,989,019 A | 6/1961 | Van Sciver, II | |
| 3,010,692 A | 11/1961 | Jentoft | |
| 3,013,234 A | 12/1961 | Bourns | |
| 3,018,791 A | 1/1962 | Knox | |
| 3,034,356 A | 5/1962 | Bieganski | |
| 3,040,800 A | 6/1962 | Hartley | |
| 3,054,618 A | 9/1962 | Abrams et al. | |
| 3,060,262 A | 10/1962 | Hoer | |
| 3,070,373 A | 12/1962 | Mathews et al. | |
| 3,082,414 A | 3/1963 | Papaminas | |
| 3,085,577 A | 4/1963 | Berman et al. | |
| 3,096,410 A | 7/1963 | Anderson | |
| 3,099,262 A | 7/1963 | Bigliano | |
| 3,125,028 A | 3/1964 | Rohde | |
| 3,126,029 A | 3/1964 | Englesson | |
| 3,129,072 A | 4/1964 | Cook et al. | |
| 3,135,914 A | 6/1964 | Callan et al. | |
| 3,144,017 A | 8/1964 | Muth | |
| 3,151,258 A | 9/1964 | Sonderegger et al. | |
| 3,153,460 A | 10/1964 | Raskin | |
| 3,161,051 A | 12/1964 | Perry, Jr. | |
| 3,167,044 A | 1/1965 | Henrickson | |
| 3,171,549 A | 3/1965 | Orloff | |
| 3,172,700 A | 3/1965 | Haas | |
| 3,173,269 A | 3/1965 | Imbertson | |

| | | | | | | |
|---|---|---|---|---|---|---|
| 3,182,494 A | 5/1965 | Beatty et al. | | 3,478,344 A | 11/1969 | Schwitzgebel et al. |
| 3,187,181 A | 6/1965 | Keller | | 3,482,449 A | 12/1969 | Werner |
| 3,187,745 A | 6/1965 | Baum et al. | | 3,482,816 A | 12/1969 | Arnold |
| 3,190,388 A | 6/1965 | Moser et al. | | 3,487,959 A | 1/1970 | Pearne et al. |
| 3,205,547 A | 9/1965 | Riekse | | 3,491,842 A | 1/1970 | Delacour et al. |
| 3,208,255 A | 9/1965 | Burk | | 3,492,638 A | 1/1970 | Lane |
| 3,209,570 A | 10/1965 | Hills | | 3,502,829 A | 3/1970 | Reynolds |
| 3,221,468 A | 12/1965 | Casey | | 3,503,116 A | 3/1970 | Strack |
| 3,228,703 A | 1/1966 | Wilson | | 3,504,664 A | 4/1970 | Haddad |
| 3,229,684 A | 1/1966 | Nagumo et al. | | 3,505,808 A | 4/1970 | Eschle |
| 3,236,088 A | 2/1966 | Moller | | 3,509,754 A | 5/1970 | Massingill et al. |
| 3,238,624 A | 3/1966 | McCabe | | 3,512,517 A | 5/1970 | Kadish et al. |
| 3,240,510 A | 3/1966 | Spouge | | 3,514,919 A | 6/1970 | Ashton et al. |
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,489 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison et al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper et al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley et al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine et al. |
| 3,463,338 A | 8/1969 | Schneider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,616 A | 4/1973 | Lenzkes |
| 3,472,230 A | 10/1969 | Fogarty | | 3,730,174 A | 5/1973 | Madison |

| | | | | | |
|---|---|---|---|---|---|
| 3,730,560 A | 5/1973 | Abildgaard et al. | 3,904,234 A | 9/1975 | Hill et al. |
| 3,731,679 A | 5/1973 | Wilhelmson et al. | 3,908,334 A | 9/1975 | Rychiger et al. |
| 3,731,681 A | 5/1973 | Blackshear et al. | 3,908,461 A | 9/1975 | Turpen |
| 3,732,731 A | 5/1973 | Fussell, Jr. | 3,908,721 A | 9/1975 | McGahey et al. |
| 3,735,040 A | 5/1973 | Punt et al. | 3,910,087 A | 10/1975 | Jones |
| 3,736,930 A | 6/1973 | Georgi | 3,912,168 A | 10/1975 | Mullins et al. |
| 3,738,356 A | 6/1973 | Workman | 3,912,304 A | 10/1975 | Abildgaard et al. |
| 3,740,921 A | 6/1973 | Meyer et al. | 3,918,286 A | 11/1975 | Whitehead |
| 3,746,111 A | 7/1973 | Berthiaume et al. | 3,918,291 A | 11/1975 | Pauly et al. |
| 3,748,678 A | 7/1973 | Ballou | 3,920,965 A | 11/1975 | Sohrwardy et al. |
| 3,749,098 A | 7/1973 | De Bennetot et al. | 3,921,682 A | 11/1975 | McGahey et al. |
| 3,749,422 A | 7/1973 | Abildgaard et al. | 3,922,951 A | 12/1975 | Linsinger et al. |
| 3,749,423 A | 7/1973 | Abildgaard et al. | 3,923,060 A | 12/1975 | Ellinwood, Jr. |
| 3,750,194 A | 8/1973 | Summers | 3,924,635 A | 12/1975 | Hakim et al. |
| 3,757,770 A | 9/1973 | Brayshaw et al. | 3,928,980 A | 12/1975 | Ganzinotti et al. |
| 3,759,095 A | 9/1973 | Short, Jr. et al. | 3,929,175 A | 12/1975 | Coone |
| 3,760,638 A | 9/1973 | Lawson et al. | 3,930,682 A | 1/1976 | Booth |
| 3,763,960 A | 10/1973 | John et al. | 3,930,852 A | 1/1976 | Tanaka et al. |
| 3,765,142 A | 10/1973 | Lindquist et al. | 3,936,028 A | 2/1976 | Norton et al. |
| 3,765,494 A | 10/1973 | Kielman, Jr. | 3,939,823 A | 2/1976 | Kaye et al. |
| 3,769,156 A | 10/1973 | Brecy et al. | 3,940,122 A | 2/1976 | Janzen et al. |
| 3,769,830 A | 11/1973 | Porter et al. | 3,940,630 A | 2/1976 | Bergonz |
| 3,774,243 A | 11/1973 | Ny et al. | 3,942,299 A | 3/1976 | Bory et al. |
| 3,776,333 A | 12/1973 | Mathauser | 3,942,382 A | 3/1976 | Hok et al. |
| 3,778,051 A | 12/1973 | Allen et al. | 3,942,536 A | 3/1976 | Mirowski et al. |
| 3,780,578 A | 12/1973 | Sellman et al. | 3,943,915 A | 3/1976 | Severson |
| 3,781,902 A | 12/1973 | Shim et al. | 3,945,704 A | 3/1976 | Kraus et al. |
| 3,783,585 A | 1/1974 | Hoyland et al. | 3,946,613 A | 3/1976 | Silver |
| 3,789,667 A | 2/1974 | Porter et al. | 3,946,615 A | 3/1976 | Hluchan |
| 3,796,095 A | 3/1974 | Fussell, Jr. | 3,946,724 A | 3/1976 | La Balme et al. |
| 3,807,219 A | 4/1974 | Wallskog | 3,948,141 A | 4/1976 | Shinjo et al. |
| 3,811,429 A | 5/1974 | Fletcher et al. | 3,949,388 A | 4/1976 | Fuller |
| 3,815,722 A | 6/1974 | Sessoms | 3,953,289 A | 4/1976 | Costes et al. |
| 3,818,765 A | 6/1974 | Eriksen et al. | 3,954,271 A | 5/1976 | Tredway, Sr. |
| 3,820,400 A | 6/1974 | Russo | 3,958,558 A | 5/1976 | Dunphy et al. |
| 3,820,795 A | 6/1974 | Taylor | 3,960,142 A | 6/1976 | Elliott et al. |
| 3,823,610 A | 7/1974 | Fussell, Jr. | 3,961,425 A | 6/1976 | Swanson et al. |
| 3,825,065 A | 7/1974 | Lloyd et al. | 3,961,646 A | 6/1976 | Schon et al. |
| 3,825,963 A | 7/1974 | Abildgaard et al. | 3,962,895 A | 6/1976 | Rydell |
| 3,825,964 A | 7/1974 | Groswith, III et al. | 3,962,921 A | 6/1976 | Lips |
| 3,828,672 A | 8/1974 | Gazzola et al. | 3,963,019 A | 6/1976 | Quandt |
| 3,828,766 A | 8/1974 | Krasnow | 3,964,485 A | 6/1976 | Neumeier |
| 3,831,588 A | 8/1974 | Rindner | 3,964,770 A | 6/1976 | Abildgaard et al. |
| 3,831,942 A | 8/1974 | Del Mar | 3,967,737 A | 7/1976 | Peralta et al. |
| 3,833,238 A | 9/1974 | Liard et al. | 3,968,473 A | 7/1976 | Patton et al. |
| 3,834,167 A | 9/1974 | Tabor | 3,968,594 A | 7/1976 | Kawakami |
| 3,834,739 A | 9/1974 | Abildgaard et al. | 3,972,320 A | 8/1976 | Kalman |
| 3,835,523 A | 9/1974 | Stansfield et al. | 3,973,753 A | 8/1976 | Wheeler |
| 3,839,708 A | 10/1974 | Bredesen et al. | 3,973,858 A | 8/1976 | Poisson et al. |
| 3,842,483 A | 10/1974 | Cramer | 3,974,655 A | 8/1976 | Halpern et al. |
| 3,842,668 A | 10/1974 | Lippke et al. | 3,974,865 A | 8/1976 | Fenton et al. |
| 3,845,664 A | 11/1974 | Perry, Jr. | 3,976,278 A | 8/1976 | Dye et al. |
| 3,845,751 A | 11/1974 | Runstetler | 3,977,391 A | 8/1976 | Fleischmann |
| 3,845,757 A | 11/1974 | Weyer | 3,980,871 A | 9/1976 | Lindstrom et al. |
| 3,847,434 A | 11/1974 | Weman et al. | 3,982,571 A | 9/1976 | Fenton et al. |
| 3,850,208 A | 11/1974 | Hamilton | 3,983,948 A | 10/1976 | Jeter |
| 3,853,117 A | 12/1974 | Murr | 3,985,133 A | 10/1976 | Jenkins et al. |
| 3,854,469 A | 12/1974 | Giori et al. | 3,987,860 A | 10/1976 | Jabsen |
| 3,855,902 A | 12/1974 | Kirst et al. | 3,989,005 A | 11/1976 | Bowler, Jr. et al. |
| 3,857,399 A | 12/1974 | Zacouto et al. | 3,991,749 A | 11/1976 | Zent |
| 3,857,452 A | 12/1974 | Hartman | 3,992,948 A | 11/1976 | D'Antonio et al. |
| 3,857,745 A | 12/1974 | Grausch et al. | 3,993,149 A | 11/1976 | Harvey |
| 3,858,581 A | 1/1975 | Kamen | 3,996,927 A | 12/1976 | Frank |
| 3,863,622 A | 2/1975 | Buuck | 3,996,962 A | 12/1976 | Sutherland |
| 3,863,933 A | 2/1975 | Tredway | 4,003,141 A | 1/1977 | Le Roy |
| 3,867,950 A | 2/1975 | Fischell | 4,005,282 A | 1/1977 | Jennings |
| 3,868,008 A | 2/1975 | Brumbaugh | 4,005,593 A | 2/1977 | Goldberg |
| 3,868,679 A | 2/1975 | Arneson | 4,006,735 A | 2/1977 | Hittman et al. |
| 3,871,599 A | 3/1975 | Takada et al. | 4,009,591 A | 3/1977 | Hester |
| 3,872,285 A | 3/1975 | Shum et al. | 4,010,449 A | 3/1977 | Faggin et al. |
| 3,874,388 A | 4/1975 | King et al. | 4,014,319 A | 3/1977 | Favre et al. |
| 3,876,980 A | 4/1975 | Haemmig et al. | 4,014,321 A | 3/1977 | March |
| 3,878,908 A | 4/1975 | Andersson et al. | 4,016,764 A | 4/1977 | Rice |
| 3,881,528 A | 5/1975 | Mackenzie | 4,017,329 A | 4/1977 | Larson |
| 3,886,948 A | 6/1975 | Hakim et al. | 4,018,134 A | 4/1977 | Linsinger et al. |
| 3,893,111 A | 7/1975 | Cotter | 4,022,190 A | 5/1977 | Meyer |
| 3,893,451 A | 7/1975 | Durand et al. | 4,024,864 A | 5/1977 | Davies et al. |
| 3,895,681 A | 7/1975 | Griffin et al. | 4,025,912 A | 5/1977 | Rice |
| 3,899,862 A | 8/1975 | Muys et al. | 4,026,276 A | 5/1977 | Chubbuck |

| | | | | | |
|---|---|---|---|---|---|
| 4,027,661 A | 6/1977 | Lyon et al. | 4,153,085 A | 5/1979 | Adams |
| 4,031,899 A | 6/1977 | Renirie et al. | 4,156,422 A | 5/1979 | Hildebrandt et al. |
| 4,036,775 A | 7/1977 | Trautvetter et al. | 4,160,448 A | 7/1979 | Jackson |
| 4,039,069 A | 8/1977 | Kwan et al. | 4,160,971 A | 7/1979 | Jones et al. |
| 4,041,954 A | 8/1977 | Ohara et al. | 4,166,469 A | 9/1979 | Littleford |
| 4,042,504 A | 8/1977 | Drori et al. | 4,167,304 A | 9/1979 | Gelbke |
| 4,045,345 A | 8/1977 | Drori et al. | 4,167,952 A | 9/1979 | Reinicke |
| 4,047,296 A | 9/1977 | Ishida et al. | 4,168,567 A | 9/1979 | Leguy et al. |
| 4,047,851 A | 9/1977 | Bender | 4,170,280 A | 10/1979 | Schwarz |
| 4,048,494 A | 9/1977 | Liesting et al. | 4,171,218 A | 10/1979 | Hoshino et al. |
| 4,048,879 A | 9/1977 | Cox | 4,173,228 A | 11/1979 | Van Steenwyk et al. |
| 4,049,004 A | 9/1977 | Walters | 4,183,124 A | 1/1980 | Hoffman |
| 4,051,338 A | 9/1977 | Harris, III | 4,183,247 A | 1/1980 | Allen et al. |
| 4,052,991 A | 10/1977 | Zacouto et al. | 4,185,641 A | 1/1980 | Minior et al. |
| 4,055,074 A | 10/1977 | Thimons et al. | 4,186,287 A | 1/1980 | Scott |
| 4,055,175 A | 10/1977 | Clemens et al. | 4,186,749 A | 2/1980 | Fryer |
| 4,056,854 A | 11/1977 | Boretos et al. | 4,186,751 A | 2/1980 | Fleischmann |
| 4,058,007 A | 11/1977 | Exner et al. | 4,190,057 A | 2/1980 | Hill et al. |
| 4,062,351 A | 12/1977 | Hastwell et al. | 4,191,004 A | 3/1980 | Gmuer et al. |
| 4,062,354 A | 12/1977 | Taylor et al. | 4,191,187 A | 3/1980 | Wright et al. |
| 4,062,360 A | 12/1977 | Bentley | 4,192,192 A | 3/1980 | Schnell |
| 4,063,439 A | 12/1977 | Besson et al. | 4,193,397 A | 3/1980 | Tucker et al. |
| 4,064,879 A * | 12/1977 | Leibinsohn .................. 604/121 | 4,204,547 A | 5/1980 | Allocca |
| 4,064,882 A | 12/1977 | Johnson et al. | 4,206,755 A | 6/1980 | Klein et al. |
| 4,070,239 A | 1/1978 | Bevilacqua | 4,206,761 A | 6/1980 | Cosman |
| 4,072,047 A | 2/1978 | Reismuller et al. | 4,206,762 A | 6/1980 | Cosman |
| 4,073,292 A | 2/1978 | Edelman | 4,207,903 A | 6/1980 | O'Neill |
| 4,075,099 A | 2/1978 | Pelton et al. | 4,212,074 A | 7/1980 | Kuno et al. |
| 4,075,602 A | 2/1978 | Clothier | 4,217,221 A | 8/1980 | Masso |
| 4,077,072 A | 3/1978 | Dezura et al. | 4,217,588 A | 8/1980 | Freeny, Jr. |
| 4,077,394 A | 3/1978 | McCurdy | 4,220,189 A | 9/1980 | Marquez |
| 4,077,405 A | 3/1978 | Haerten et al. | 4,221,219 A | 9/1980 | Tucker |
| 4,077,882 A | 3/1978 | Gangemi | 4,221,523 A | 9/1980 | Eberle |
| 4,078,620 A | 3/1978 | Westlake et al. | 4,223,837 A | 9/1980 | Gubbiotti et al. |
| 4,080,653 A | 3/1978 | Barnes, Jr. et al. | 4,226,124 A | 10/1980 | Kersten et al. |
| 4,084,752 A | 4/1978 | Hagiwara et al. | 4,226,229 A | 10/1980 | Eckhart et al. |
| 4,086,488 A | 4/1978 | Hill | 4,227,533 A | 10/1980 | Godfrey |
| 4,087,568 A | 5/1978 | Fay et al. | 4,231,376 A | 11/1980 | Lyon et al. |
| 4,088,417 A | 5/1978 | Kosmowski | 4,232,682 A | 11/1980 | Veth |
| 4,089,329 A | 5/1978 | Couvillon, Jr. et al. | 4,237,900 A | 12/1980 | Schulman et al. |
| 4,090,802 A | 5/1978 | Bilz et al. | 4,241,247 A | 12/1980 | Byrne et al. |
| 4,092,719 A | 5/1978 | Salmon et al. | 4,241,870 A | 12/1980 | Marcus |
| 4,092,925 A | 6/1978 | Fromson | 4,245,593 A | 1/1981 | Stein |
| 4,096,866 A | 6/1978 | Fischell | 4,246,877 A | 1/1981 | Kennedy |
| 4,098,293 A | 7/1978 | Kramer et al. | 4,247,850 A | 1/1981 | Marcus |
| 4,103,496 A | 8/1978 | Colamussi et al. | 4,248,238 A | 2/1981 | Joseph et al. |
| 4,106,370 A | 8/1978 | Kraus et al. | 4,248,241 A | 2/1981 | Tacchi |
| 4,107,689 A | 8/1978 | Jellinek | 4,256,094 A | 3/1981 | Kapp et al. |
| 4,107,995 A | 8/1978 | Ligman et al. | 4,256,118 A | 3/1981 | Nagel et al. |
| 4,108,148 A | 8/1978 | Cannon, III | 4,262,343 A | 4/1981 | Claycomb |
| 4,108,575 A | 8/1978 | Schal et al. | 4,262,632 A | 4/1981 | Hanton et al. |
| 4,109,148 A | 8/1978 | Jaulmes et al. | 4,265,241 A | 5/1981 | Portner et al. |
| 4,109,518 A | 8/1978 | Dooley et al. | 4,265,252 A | 5/1981 | Chubbuck et al. |
| 4,109,644 A | 8/1978 | Kojima | 4,271,018 A | 6/1981 | Drori et al. |
| 4,111,056 A | 9/1978 | Mastromatteo | 4,273,070 A | 6/1981 | Hoefelmayr et al. |
| 4,111,629 A | 9/1978 | Nussbaumer et al. | 4,274,444 A | 6/1981 | Ruyak |
| 4,114,424 A | 9/1978 | Johnson | 4,275,600 A | 6/1981 | Turner et al. |
| 4,114,603 A | 9/1978 | Wilkinson | 4,275,913 A | 6/1981 | Marcus |
| 4,114,606 A | 9/1978 | Seylar | 4,278,540 A | 7/1981 | Drori et al. |
| 4,120,097 A | 10/1978 | Jeter | 4,280,036 A | 7/1981 | Fukatsu et al. |
| 4,120,134 A | 10/1978 | Scholle | 4,280,775 A | 7/1981 | Wood |
| 4,121,635 A | 10/1978 | Hansel | 4,281,666 A | 8/1981 | Cosman |
| 4,123,310 A | 10/1978 | Varon et al. | 4,281,667 A | 8/1981 | Cosman |
| 4,124,023 A | 11/1978 | Fleischmann et al. | 4,284,073 A | 8/1981 | Krause et al. |
| 4,127,110 A | 11/1978 | Bullara | 4,285,770 A | 8/1981 | Chi et al. |
| 4,130,169 A | 12/1978 | Denison | 4,291,699 A | 9/1981 | Geddes et al. |
| 4,131,596 A | 12/1978 | Allen | 4,295,963 A | 10/1981 | Drori et al. |
| 4,133,355 A | 1/1979 | Mayer | 4,297,927 A | 11/1981 | Kuroda et al. |
| 4,133,367 A | 1/1979 | Abell | 4,303,075 A | 12/1981 | Heilman et al. |
| 4,135,509 A | 1/1979 | Shannon | 4,305,402 A | 12/1981 | Katims |
| 4,140,131 A | 2/1979 | Dutcher et al. | 4,312,374 A | 1/1982 | Drori et al. |
| 4,141,348 A | 2/1979 | Hittman | 4,314,480 A | 2/1982 | Becker |
| 4,141,349 A | 2/1979 | Ory et al. | 4,316,693 A | 2/1982 | Baxter et al. |
| 4,143,661 A | 3/1979 | LaForge et al. | 4,325,387 A | 4/1982 | Helfer |
| 4,146,029 A | 3/1979 | Ellinwood, Jr. | 4,327,804 A | 5/1982 | Reed |
| 4,147,161 A | 4/1979 | Ikebe et al. | 4,328,654 A | 5/1982 | Van Ginkel et al. |
| 4,148,096 A | 4/1979 | Haas et al. | 4,332,254 A | 6/1982 | Lundquist |
| 4,149,423 A | 4/1979 | Frosch et al. | 4,332,255 A | 6/1982 | Hakim et al. |
| 4,151,823 A | 5/1979 | Grosse et al. | 4,339,831 A | 7/1982 | Johnson |

| | | | | | |
|---|---|---|---|---|---|
| 4,342,218 A | 8/1982 | Fox | 4,468,762 A | 8/1984 | Jurgens et al. |
| 4,342,308 A | 8/1982 | Trick | 4,469,365 A | 9/1984 | Marcus et al. |
| 4,346,604 A | 8/1982 | Snook et al. | 4,471,182 A | 9/1984 | Wielgos et al. |
| 4,347,851 A | 9/1982 | Jundaniam | 4,471,786 A | 9/1984 | Inagaki et al. |
| 4,350,647 A | 9/1982 | de la Cruz | 4,473,067 A | 9/1984 | Schiff |
| 4,350,970 A | 9/1982 | von Tomkewitsch et al. | 4,473,078 A | 9/1984 | Angel |
| 4,351,037 A | 9/1982 | Scherbatskoy | 4,476,721 A | 10/1984 | Hochreuther et al. |
| 4,351,116 A | 9/1982 | Scott, Jr. | 4,478,213 A | 10/1984 | Redding |
| 4,356,486 A | 10/1982 | Mount | 4,478,538 A | 10/1984 | Kakino et al. |
| 4,360,010 A | 11/1982 | Finney | 4,483,196 A | 11/1984 | Kurtz et al. |
| 4,360,277 A | 11/1982 | Daniel et al. | 4,484,135 A | 11/1984 | Ishihara et al. |
| 4,361,153 A | 11/1982 | Slocum et al. | 4,485,813 A | 12/1984 | Anderson et al. |
| 4,363,236 A | 12/1982 | Meyers | 4,489,916 A | 12/1984 | Stevens |
| 4,364,276 A | 12/1982 | Shimazoe et al. | 4,492,632 A | 1/1985 | Mattson |
| 4,365,425 A | 12/1982 | Gotchel | 4,494,411 A | 1/1985 | Koschke et al. |
| 4,368,937 A | 1/1983 | Palombo et al. | 4,494,950 A | 1/1985 | Fischell |
| 4,369,013 A | 1/1983 | Abildgaard et al. | 4,497,176 A | 2/1985 | Rubin et al. |
| 4,373,527 A | 2/1983 | Fischell | 4,497,201 A | 2/1985 | Allen et al. |
| 4,376,523 A | 3/1983 | Goyen et al. | 4,499,394 A | 2/1985 | Koal |
| 4,378,809 A | 4/1983 | Cosman | 4,499,691 A | 2/1985 | Karazim et al. |
| 4,380,427 A | 4/1983 | Hehl et al. | 4,499,750 A | 2/1985 | Gerber et al. |
| 4,385,636 A | 5/1983 | Cosman | 4,503,678 A | 3/1985 | Wimbush et al. |
| 4,386,422 A | 5/1983 | Mumby et al. | 4,511,974 A | 4/1985 | Nakane et al. |
| 4,387,715 A | 6/1983 | Hakim et al. | 4,513,295 A | 4/1985 | Jones et al. |
| 4,387,907 A | 6/1983 | Hiestand et al. | 4,515,004 A | 5/1985 | Jaenson |
| 4,392,368 A | 7/1983 | Folkesson et al. | 4,515,750 A | 5/1985 | Pardini et al. |
| 4,393,899 A | 7/1983 | Tsuji et al. | 4,516,866 A | 5/1985 | Yamauchi et al. |
| 4,393,951 A | 7/1983 | Horst-Rudolf et al. | 4,518,637 A | 5/1985 | Takeda et al. |
| 4,395,232 A | 7/1983 | Koch | 4,519,401 A | 5/1985 | Ko et al. |
| 4,395,258 A | 7/1983 | Wang et al. | 4,520,443 A | 5/1985 | Yuki et al. |
| 4,395,916 A | 8/1983 | Martin | 4,522,213 A | 6/1985 | Wallroth et al. |
| 4,398,983 A | 8/1983 | Suzuki et al. | 4,527,568 A | 7/1985 | Rickards et al. |
| 4,399,705 A | 8/1983 | Weiger et al. | 4,529,401 A | 7/1985 | Leslie et al. |
| 4,399,707 A | 8/1983 | Wamstad | 4,531,526 A | 7/1985 | Genest |
| 4,399,809 A | 8/1983 | Baro et al. | 4,531,936 A | 7/1985 | Gordon |
| 4,399,821 A | 8/1983 | Bowers | 4,536,000 A | 8/1985 | Rohm et al. |
| 4,403,984 A | 9/1983 | Ash et al. | 4,537,005 A | 8/1985 | Hoyland et al. |
| 4,404,968 A | 9/1983 | Evans, Sr. | 4,537,129 A | 8/1985 | Heinemann et al. |
| 4,404,974 A | 9/1983 | Titus | 4,538,616 A | 9/1985 | Rogoff |
| 4,405,318 A | 9/1983 | Whitney et al. | 4,540,404 A | 9/1985 | Wolvek |
| 4,407,125 A | 10/1983 | Parsons et al. | 4,542,461 A | 9/1985 | Eldridge et al. |
| 4,407,271 A | 10/1983 | Schiff | 4,544,369 A | 10/1985 | Skakoon et al. |
| 4,407,296 A | 10/1983 | Anderson | 4,545,185 A | 10/1985 | Chikatani et al. |
| 4,407,326 A | 10/1983 | Wilhelm | 4,546,524 A | 10/1985 | Kreft |
| 4,408,597 A | 10/1983 | Tenney, Jr. | 4,548,209 A | 10/1985 | Wielders et al. |
| 4,415,071 A | 11/1983 | Butler et al. | 4,551,128 A | 11/1985 | Hakim et al. |
| 4,416,282 A | 11/1983 | Saulson et al. | 4,552,150 A | 11/1985 | Zacouto et al. |
| 4,418,899 A | 12/1983 | Zimmermann et al. | 4,553,226 A | 11/1985 | Scherbatskoy |
| 4,419,393 A | 12/1983 | Hanson et al. | 4,556,063 A | 12/1985 | Thompson et al. |
| 4,421,124 A | 12/1983 | Marshall | 4,556,086 A | 12/1985 | Raines |
| 4,421,505 A | 12/1983 | Schwartz | 4,557,269 A | 12/1985 | Reynolds et al. |
| 4,424,720 A | 1/1984 | Bucchianeri | 4,557,332 A | 12/1985 | Denison et al. |
| 4,428,228 A | 1/1984 | Banzhaf et al. | 4,559,815 A | 12/1985 | Needham et al. |
| 4,428,365 A | 1/1984 | Hakky et al. | 4,560,979 A | 12/1985 | Rosskopf et al. |
| 4,430,899 A | 2/1984 | Wessel et al. | 4,561,442 A | 12/1985 | Vollmann et al. |
| 4,431,009 A | 2/1984 | Marino, Jr. et al. | 4,562,751 A | 1/1986 | Nason et al. |
| 4,431,365 A | 2/1984 | Sturtz, Jr. | 4,563,175 A | 1/1986 | LaFond |
| 4,432,363 A | 2/1984 | Kakegawa et al. | 4,565,116 A | 1/1986 | Hehl et al. |
| 4,435,173 A | 3/1984 | Siposs et al. | 4,566,456 A | 1/1986 | Koning et al. |
| 4,439,186 A | 3/1984 | Kuhl et al. | 4,569,623 A | 2/1986 | Goldmann |
| 4,441,491 A | 4/1984 | Evans, Sr. | 4,570,351 A | 2/1986 | Szanto et al. |
| 4,441,501 A | 4/1984 | Parent | 4,571,161 A | 2/1986 | Leblanc et al. |
| 4,444,194 A | 4/1984 | Burcham | 4,571,749 A | 2/1986 | Fischell |
| 4,444,498 A | 4/1984 | Heinemann | 4,571,995 A | 2/1986 | Timme |
| 4,445,385 A | 5/1984 | Endo | 4,573,835 A | 3/1986 | Eckardt et al. |
| 4,446,711 A | 5/1984 | Valente | 4,574,792 A | 3/1986 | Trick |
| 4,447,224 A | 5/1984 | DeCant, Jr. et al. | 4,576,181 A | 3/1986 | Wallace et al. |
| 4,449,493 A | 5/1984 | Kopec et al. | 4,576,183 A | 3/1986 | Plicchi et al. |
| 4,450,811 A | 5/1984 | Ichikawa et al. | 4,577,512 A | 3/1986 | Lowenheck et al. |
| 4,450,946 A | 5/1984 | Olding et al. | 4,581,018 A | 4/1986 | Jassawalla et al. |
| 4,451,033 A | 5/1984 | Nestegard | 4,581,915 A | 4/1986 | Haulsee et al. |
| 4,453,537 A | 6/1984 | Spitzer | 4,587,840 A | 5/1986 | Dobler et al. |
| 4,453,578 A | 6/1984 | Wilder | 4,589,805 A | 5/1986 | Duffner et al. |
| 4,460,835 A | 7/1984 | Masuoka et al. | 4,592,339 A | 6/1986 | Kuzmak et al. |
| 4,464,170 A | 8/1984 | Clemens et al. | 4,592,340 A | 6/1986 | Boyles |
| 4,465,015 A | 8/1984 | Osta et al. | 4,593,703 A | 6/1986 | Cosman |
| 4,465,474 A | 8/1984 | Mardorf et al. | 4,595,228 A | 6/1986 | Chu |
| 4,466,290 A | 8/1984 | Frick | 4,595,390 A | 6/1986 | Hakim et al. |
| 4,468,172 A | 8/1984 | Dixon et al. | 4,596,563 A | 6/1986 | Pande |

| | | | | | | |
|---|---|---|---|---|---|---|
| 4,599,943 | A | 7/1986 | Kobler et al. | 4,752,658 A | 6/1988 | Mack |
| 4,600,855 | A | 7/1986 | Strachan et al. | 4,757,463 A | 7/1988 | Ballou et al. |
| 4,602,541 | A | 7/1986 | Benzinger et al. | 4,759,386 A | 7/1988 | Grouw, III |
| 4,604,089 | A | 8/1986 | Santangelo et al. | 4,763,649 A | 8/1988 | Merrick |
| 4,605,354 | A | 8/1986 | Daly | 4,765,001 A | 8/1988 | Smith |
| 4,606,419 | A | 8/1986 | Perini | 4,767,406 A | 8/1988 | Wadham et al. |
| 4,606,478 | A | 8/1986 | Hack et al. | 4,769,001 A | 9/1988 | Prince |
| 4,610,256 | A | 9/1986 | Wallace | 4,772,257 A | 9/1988 | Hakim et al. |
| 4,614,137 | A | 9/1986 | Jones | 4,772,896 A | 9/1988 | Nakatsu et al. |
| 4,615,691 | A | 10/1986 | Hakim et al. | 4,773,401 A | 9/1988 | Citak et al. |
| 4,617,016 | A | 10/1986 | Blomberg et al. | 4,774,950 A | 10/1988 | Cohen |
| 4,618,861 | A | 10/1986 | Gettens et al. | 4,774,955 A | 10/1988 | Jones |
| 4,620,807 | A | 11/1986 | Polit | 4,777,953 A | 10/1988 | Ash et al. |
| 4,621,331 | A | 11/1986 | Iwata et al. | 4,779,626 A | 10/1988 | Peel et al. |
| 4,622,871 | A | 11/1986 | Van Sickle et al. | 4,781,192 A | 11/1988 | Demer |
| 4,626,462 | A | 12/1986 | Kober et al. | 4,782,826 A | 11/1988 | Fogarty |
| 4,633,304 | A | 12/1986 | Nagasaki et al. | 4,783,106 A | 11/1988 | Nutter |
| 4,633,878 | A | 1/1987 | Bombardieri et al. | 4,785,822 A | 11/1988 | Wallace |
| 4,635,182 | A | 1/1987 | Hintz | 4,788,847 A | 12/1988 | Sterghos |
| 4,637,736 | A | 1/1987 | Andeen et al. | 4,791,318 A | 12/1988 | Lewis et al. |
| 4,638,665 | A | 1/1987 | Benson et al. | 4,794,803 A | 1/1989 | Osterhout et al. |
| 4,644,246 | A | 2/1987 | Knapen et al. | 4,796,641 A | 1/1989 | Mills et al. |
| 4,646,553 | A | 3/1987 | Tufte et al. | 4,798,211 A | 1/1989 | Goor et al. |
| 4,648,363 | A | 3/1987 | Kronich | 4,798,227 A | 1/1989 | Goodwin |
| 4,648,406 | A | 3/1987 | Miller | 4,799,491 A | 1/1989 | Eckerle |
| 4,658,358 | A | 4/1987 | Leach et al. | 4,799,625 A | 1/1989 | Weaver, Jr. et al. |
| 4,658,760 | A | 4/1987 | Zebuhr | 4,802,488 A | 2/1989 | Eckerle |
| 4,660,568 | A | 4/1987 | Cosman | 4,803,987 A | 2/1989 | Calfee et al. |
| 4,665,511 | A | 5/1987 | Rodney et al. | 4,804,368 A | 2/1989 | Skakoon et al. |
| 4,665,896 | A | 5/1987 | LaForge et al. | 4,807,321 A | 2/1989 | Grasselli et al. |
| 4,669,484 | A | 6/1987 | Masters | 4,808,167 A | 2/1989 | Mann et al. |
| 4,672,974 | A | 6/1987 | Lee | 4,812,823 A | 3/1989 | Dickerson |
| 4,674,457 | A | 6/1987 | Berger et al. | 4,819,656 A | 4/1989 | Spector |
| 4,674,546 | A | 6/1987 | Fournier et al. | 4,820,265 A | 4/1989 | DeSatnick et al. |
| 4,678,408 | A | 7/1987 | Nason et al. | 4,820,953 A | 4/1989 | Saubolle et al. |
| 4,681,559 | A | 7/1987 | Hooven | 4,821,167 A | 4/1989 | Wiebe |
| 4,683,850 | A | 8/1987 | Bauder et al. | 4,821,723 A | 4/1989 | Baker, Jr. et al. |
| 4,685,463 | A | 8/1987 | Williams | 4,823,779 A | 4/1989 | Daly et al. |
| 4,685,469 | A | 8/1987 | Keller et al. | 4,830,006 A | 5/1989 | Haluska et al. |
| 4,685,903 | A | 8/1987 | Cable et al. | 4,832,034 A | 5/1989 | Pizziconi et al. |
| 4,686,987 | A | 8/1987 | Salo et al. | 4,833,384 A | 5/1989 | Munro et al. |
| 4,687,530 | A | 8/1987 | Berscheid et al. | 4,834,731 A | 5/1989 | Nowak et al. |
| 4,691,694 | A | 9/1987 | Boyd et al. | 4,838,857 A | 6/1989 | Strowe et al. |
| 4,691,710 | A | 9/1987 | Dickens et al. | 4,840,068 A | 6/1989 | Mayhew, Jr. |
| 4,693,253 | A | 9/1987 | Adams | 4,840,350 A | 6/1989 | Cook et al. |
| 4,695,237 | A | 9/1987 | Inaba et al. | 4,844,002 A | 7/1989 | Yasue et al. |
| 4,696,189 | A | 9/1987 | Hochreuther et al. | 4,846,153 A | 7/1989 | Berci |
| 4,697,574 | A | 10/1987 | Karcher et al. | 4,846,191 A | 7/1989 | Brockway et al. |
| 4,698,038 | A | 10/1987 | Key et al. | 4,846,664 A | 7/1989 | Hehl et al. |
| 4,700,497 | A | 10/1987 | Sato et al. | 4,854,328 A | 8/1989 | Pollack |
| 4,700,610 | A | 10/1987 | Bauer et al. | 4,863,470 A | 9/1989 | Carter |
| 4,701,143 | A | 10/1987 | Key et al. | 4,865,587 A | 9/1989 | Walling |
| 4,703,756 | A | 11/1987 | Gough et al. | 4,867,160 A | 9/1989 | Schaldach et al. |
| 4,705,507 | A | 11/1987 | Boyles | 4,867,498 A | 9/1989 | Delphia et al. |
| 4,706,948 | A | 11/1987 | Kroecher et al. | 4,867,618 A | 9/1989 | Brohammer |
| 4,711,249 | A | 12/1987 | Brooks | 4,869,252 A | 9/1989 | Gilli |
| 4,712,562 | A | 12/1987 | Ohayon et al. | 4,870,258 A | 9/1989 | Mochizuki et al. |
| 4,718,425 | A | 1/1988 | Tanaka et al. | 4,871,351 A | 10/1989 | Feingold et al. |
| 4,722,348 | A | 2/1988 | Ligtenberg et al. | 4,872,483 A | 10/1989 | Shah |
| 4,724,806 | A | 2/1988 | Hartwig et al. | 4,872,869 A | 10/1989 | Johns |
| 4,724,830 | A | 2/1988 | Fischell | 4,873,677 A | 10/1989 | Sakamoto et al. |
| 4,725,826 | A | 2/1988 | Hunter | 4,875,483 A | 10/1989 | Vollmann et al. |
| 4,727,887 | A | 3/1988 | Haber | 4,880,004 A | 11/1989 | Baker, Jr. et al. |
| 4,728,479 | A | 3/1988 | Merkovsky | 4,882,678 A | 11/1989 | Hollis et al. |
| 4,729,517 | A | 3/1988 | Krokor et al. | 4,886,392 A | 12/1989 | Iio et al. |
| 4,730,188 | A | 3/1988 | Milheiser | 4,893,630 A | 1/1990 | Bray, Jr. |
| 4,730,420 | A | 3/1988 | Stratmann et al. | 4,895,151 A | 1/1990 | Grevis et al. |
| 4,730,619 | A | 3/1988 | Koning et al. | 4,896,594 A | 1/1990 | Baur et al. |
| 4,731,058 | A | 3/1988 | Doan | 4,898,158 A | 2/1990 | Daly et al. |
| 4,735,205 | A | 4/1988 | Chachques et al. | 4,898,578 A | 2/1990 | Rubalcaba, Jr. |
| 4,738,267 | A | 4/1988 | Lazorthes et al. | 4,899,751 A | 2/1990 | Cohen |
| 4,738,268 | A | 4/1988 | Kipnis | 4,899,752 A | 2/1990 | Cohen |
| 4,741,345 | A | 5/1988 | Matthews et al. | 4,902,277 A | 2/1990 | Mathies et al. |
| 4,741,732 | A | 5/1988 | Crankshaw et al. | 4,903,701 A | 2/1990 | Moore et al. |
| 4,743,129 | A | 5/1988 | Keryhuel et al. | 4,905,698 A | 3/1990 | Strohl, Jr. et al. |
| 4,745,541 | A | 5/1988 | Vaniglia et al. | 4,909,678 A | 3/1990 | Kakimoto et al. |
| 4,746,830 | A | 5/1988 | Holland | 4,913,147 A | 4/1990 | Fahlstrom et al. |
| 4,750,495 | A | 6/1988 | Moore et al. | 4,919,143 A | 4/1990 | Ayers |
| 4,752,115 | A | 6/1988 | Murray, Jr. et al. | 4,924,872 A | 5/1990 | Frank |

| Patent No. | Date | Inventor(s) |
|---|---|---|
| 4,926,903 A | 5/1990 | Kawai et al. |
| 4,932,406 A | 6/1990 | Berkovits |
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,006,997 A | 4/1991 | Reich |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,099,845 A | 3/1992 | Besz et al. |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,120,313 A | 6/1992 | Elftman |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,163,904 A | 11/1992 | Lampropoulos et al. |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirige et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |

| | | | | | |
|---|---|---|---|---|---|
| 5,211,129 A | 5/1993 | Taylor et al. | 5,394,909 A | 3/1995 | Mitchell et al. |
| 5,211,161 A | 5/1993 | Stef et al. | 5,396,899 A | 3/1995 | Strittmatter |
| 5,212,476 A | 5/1993 | Maloney | 5,402,944 A | 4/1995 | Pape et al. |
| 5,213,331 A | 5/1993 | Avanzini | 5,406,957 A | 4/1995 | Tansey |
| 5,215,523 A | 6/1993 | Williams et al. | 5,409,009 A | 4/1995 | Olson |
| 5,218,343 A | 6/1993 | Stobbe et al. | 5,411,031 A | 5/1995 | Yomtov |
| 5,218,957 A | 6/1993 | Strickland | 5,411,551 A | 5/1995 | Winston et al. |
| 5,226,429 A | 7/1993 | Kuzmak | 5,411,552 A | 5/1995 | Andersen et al. |
| 5,226,604 A | 7/1993 | Seiffert et al. | 5,416,372 A | 5/1995 | Ljungstroem et al. |
| 5,230,694 A | 7/1993 | Rosenblum | 5,417,226 A | 5/1995 | Juma |
| 5,233,985 A | 8/1993 | Hudrik | 5,417,717 A | 5/1995 | Salo et al. |
| 5,235,326 A | 8/1993 | Beigel et al. | 5,425,362 A | 6/1995 | Siker et al. |
| 5,244,269 A | 9/1993 | Harriehausen et al. | 5,425,713 A | 6/1995 | Taylor et al. |
| 5,244,461 A | 9/1993 | Derlien et al. | 5,431,171 A | 7/1995 | Harrison et al. |
| 5,246,008 A | 9/1993 | Mueller et al. | 5,431,629 A | 7/1995 | Lampropoulos et al. |
| 5,249,858 A | 10/1993 | Nusser | 5,431,694 A | 7/1995 | Snaper et al. |
| 5,250,020 A | 10/1993 | Bley | 5,433,694 A | 7/1995 | Lim et al. |
| 5,254,096 A | 10/1993 | Rondelet et al. | 5,437,605 A | 8/1995 | Helmy et al. |
| 5,256,157 A | 10/1993 | Samiotes et al. | 5,443,215 A | 8/1995 | Fackler |
| 5,263,244 A | 11/1993 | Centa et al. | 5,447,519 A | 9/1995 | Peterson |
| 5,263,981 A | 11/1993 | Polyak et al. | 5,449,345 A | 9/1995 | Taylor et al. |
| 5,267,940 A | 12/1993 | Moulder | 5,449,368 A | 9/1995 | Kuzmak |
| 5,267,942 A | 12/1993 | Saperston | 5,456,690 A | 10/1995 | Duong-Van |
| 5,269,891 A | 12/1993 | Colin et al. | 5,461,293 A | 10/1995 | Rozman et al. |
| 5,271,395 A | 12/1993 | Wahlstrand et al. | 5,461,390 A | 10/1995 | Hoshen |
| 5,274,859 A | 1/1994 | Redman et al. | 5,464,435 A | 11/1995 | Neumann |
| 5,280,789 A | 1/1994 | Potts | 5,467,627 A | 11/1995 | Smith et al. |
| 5,282,839 A | 2/1994 | Roline et al. | 5,474,226 A | 12/1995 | Joseph |
| 5,282,840 A | 2/1994 | Hudrlik | 5,479,818 A | 1/1996 | Walter et al. |
| 5,291,894 A | 3/1994 | Nagy et al. | 5,482,049 A | 1/1996 | Addiss et al. |
| 5,292,219 A | 3/1994 | Merin et al. | 5,487,760 A | 1/1996 | Villafana |
| 5,295,967 A | 3/1994 | Rondelet et al. | 5,490,514 A | 2/1996 | Rosenberg |
| 5,298,022 A | 3/1994 | Bernardi et al. | 5,493,738 A | 2/1996 | Sanderson et al. |
| 5,298,884 A | 3/1994 | Gilmore et al. | 5,494,036 A | 2/1996 | Uber, III et al. |
| 5,300,093 A | 4/1994 | Koestner | 5,494,193 A | 2/1996 | Kirschner et al. |
| 5,300,120 A | 4/1994 | Knapp et al. | 5,504,474 A | 4/1996 | Libman et al. |
| 5,304,112 A | 4/1994 | Mrklas et al. | 5,505,916 A | 4/1996 | Berry, Jr. |
| 5,305,923 A | 4/1994 | Kirschner et al. | 5,507,412 A | 4/1996 | Ebert et al. |
| 5,312,443 A | 5/1994 | Adams et al. | 5,507,737 A | 4/1996 | Palmskog et al. |
| 5,312,452 A | 5/1994 | Salo | 5,507,785 A | 4/1996 | Deno |
| 5,312,453 A | 5/1994 | Shelton et al. | 5,509,888 A | 4/1996 | Miller |
| 5,313,953 A | 5/1994 | Yomtov et al. | 5,509,891 A | 4/1996 | DeRidder |
| 5,314,451 A | 5/1994 | Mulier | 5,513,945 A | 5/1996 | Hartmann et al. |
| 5,314,457 A | 5/1994 | Jeutter et al. | 5,514,103 A | 5/1996 | Srisathapat et al. |
| 5,324,315 A | 6/1994 | Grevious | 5,518,504 A | 5/1996 | Polyak |
| 5,325,834 A | 7/1994 | Ballheimer et al. | 5,520,606 A | 5/1996 | Schoolman et al. |
| 5,326,249 A | 7/1994 | Weissfloch et al. | 5,523,740 A | 6/1996 | Burgmann et al. |
| 5,328,460 A | 7/1994 | Lord et al. | 5,534,018 A | 7/1996 | Wahlstrand et al. |
| 5,330,511 A | 7/1994 | Boute et al. | 5,535,752 A | 7/1996 | Halperin et al. |
| 5,337,750 A | 8/1994 | Wallock | 5,538,005 A | 7/1996 | Harrison et al. |
| 5,341,430 A | 8/1994 | Aulia et al. | 5,540,731 A | 7/1996 | Testerman |
| 5,342,401 A | 8/1994 | Spano et al. | 5,541,857 A | 7/1996 | Walter et al. |
| 5,342,406 A | 8/1994 | Thompson | 5,545,140 A | 8/1996 | Conero et al. |
| 5,344,388 A | 9/1994 | Maxwell et al. | 5,545,151 A | 8/1996 | O'Connor et al. |
| 5,347,476 A | 9/1994 | McBean, Sr. | 5,545,186 A | 8/1996 | Olson et al. |
| 5,348,210 A | 9/1994 | Linzell et al. | 5,545,214 A | 8/1996 | Stevens |
| 5,348,536 A | 9/1994 | Young et al. | 5,547,470 A | 8/1996 | Johnson et al. |
| 5,350,413 A | 9/1994 | Miller et al. | 5,551,427 A | 9/1996 | Altman |
| 5,352,180 A | 10/1994 | Candelon et al. | 5,551,439 A | 9/1996 | Hickey |
| 5,353,622 A | 10/1994 | Theener | 5,554,185 A | 9/1996 | Block et al. |
| 5,353,800 A | 10/1994 | Pohndorf et al. | 5,558,644 A | 9/1996 | Boyd et al. |
| 5,354,200 A | 10/1994 | Klein et al. | 5,564,434 A | 10/1996 | Halperin et al. |
| 5,354,316 A | 10/1994 | Keimel | 5,575,770 A | 11/1996 | Melsky et al. |
| 5,354,319 A | 10/1994 | Wyborny et al. | 5,584,803 A | 12/1996 | Stevens et al. |
| 5,360,407 A | 11/1994 | Leonard et al. | 5,586,629 A | 12/1996 | Shoberg et al. |
| 5,365,462 A | 11/1994 | McBean, Sr. | 5,591,171 A | 1/1997 | Brown |
| 5,365,619 A | 11/1994 | Solomon | 5,592,939 A | 1/1997 | Martinelli |
| 5,365,985 A | 11/1994 | Todd et al. | 5,593,430 A | 1/1997 | Renger |
| 5,368,040 A | 11/1994 | Carney | 5,594,665 A | 1/1997 | Walter et al. |
| 5,370,665 A | 12/1994 | Hudrlik | 5,596,986 A | 1/1997 | Goldfarb |
| 5,373,852 A | 12/1994 | Harrison et al. | 5,597,284 A | 1/1997 | Weltlich et al. |
| 5,375,073 A | 12/1994 | McBean | 5,610,083 A | 3/1997 | Chan et al. |
| 5,377,128 A | 12/1994 | McBean | 5,611,768 A | 3/1997 | Tutrone, Jr. |
| 5,378,231 A | 1/1995 | Johnson et al. | 5,612,497 A | 3/1997 | Walter et al. |
| 5,382,232 A | 1/1995 | Hague et al. | 5,615,671 A | 4/1997 | Schoonen et al. |
| 5,383,915 A | 1/1995 | Adams | 5,619,991 A | 4/1997 | Sloane |
| 5,388,578 A | 2/1995 | Yomtov et al. | 5,622,869 A | 4/1997 | Lewis et al. |
| 5,388,586 A | 2/1995 | Lee et al. | 5,625,946 A | 5/1997 | Wildeson et al. |
| 5,388,831 A | 2/1995 | Quadri et al. | 5,626,623 A | 5/1997 | Kieval et al. |

| | | | | | |
|---|---|---|---|---|---|
| 5,626,630 A | 5/1997 | Markowitz et al. | 5,957,861 A | 9/1999 | Combs et al. |
| 5,630,836 A | 5/1997 | Prem et al. | 5,967,986 A | 10/1999 | Cimochowski et al. |
| 5,634,255 A | 6/1997 | Bishop et al. | 5,970,801 A | 10/1999 | Ciobanu et al. |
| 5,637,083 A | 6/1997 | Bertrand et al. | 5,971,934 A | 10/1999 | Scherer et al. |
| 5,643,207 A | 7/1997 | Rise | 5,974,873 A | 11/1999 | Nelson et al. |
| 5,645,065 A | 7/1997 | Shapiro et al. | 5,978,985 A | 11/1999 | Thurman |
| 5,645,116 A | 7/1997 | McDonald | 5,991,664 A | 11/1999 | Seligman |
| 5,650,766 A | 7/1997 | Burgmann et al. | 5,993,395 A | 11/1999 | Shulze |
| 5,673,585 A | 10/1997 | Bishop et al. | 5,993,398 A | 11/1999 | Alperin |
| 5,676,690 A | 10/1997 | Noren et al. | 5,995,874 A | 11/1999 | Borza et al. |
| 5,681,285 A | 10/1997 | Ford et al. | 6,009,878 A | 1/2000 | Weijand et al. |
| 5,686,831 A | 11/1997 | Vandervalk et al. | 6,010,482 A | 1/2000 | Kriesel et al. |
| 5,687,734 A | 11/1997 | Dempsey et al. | 6,015,386 A | 1/2000 | Kensey et al. |
| 5,693,076 A | 12/1997 | Kaemmerer | 6,015,387 A | 1/2000 | Schwartz et al. |
| 5,702,368 A | 12/1997 | Stevens et al. | 6,019,729 A | 2/2000 | Itoigawa et al. |
| 5,702,427 A | 12/1997 | Ecker et al. | 6,024,704 A | 2/2000 | Meador et al. |
| 5,702,431 A | 12/1997 | Wang et al. | 6,030,413 A | 2/2000 | Lazarus |
| 5,704,352 A | 1/1998 | Tremblay et al. | 6,035,461 A | 3/2000 | Nguyen |
| 5,711,302 A | 1/1998 | Lampropoulos et al. | 6,053,873 A | 4/2000 | Govari et al. |
| 5,715,786 A | 2/1998 | Seiberth et al. | 6,056,723 A | 5/2000 | Donlon |
| 5,715,837 A | 2/1998 | Chen | 6,058,330 A | 5/2000 | Borza et al. |
| 5,716,342 A | 2/1998 | Dumbraveanu et al. | 6,059,757 A | 5/2000 | Macoviak et al. |
| 5,720,436 A | 2/1998 | Buschor et al. | 6,067,474 A | 5/2000 | Schulman et al. |
| 5,721,382 A | 2/1998 | Kriesel et al. | 6,067,991 A | 5/2000 | Forsell et al. |
| 5,730,101 A | 3/1998 | Aupperle et al. | 6,071,267 A | 6/2000 | Zamierowski |
| 5,732,710 A | 3/1998 | Rabinovich et al. | 6,076,016 A | 6/2000 | Feierbach |
| 5,733,313 A | 3/1998 | Barreras, Sr. et al. | 6,083,174 A | 7/2000 | Brehmeier-Flick et al. |
| 5,738,652 A | 4/1998 | Boyd et al. | 6,089,831 A | 7/2000 | Bruehmann et al. |
| 5,742,233 A | 4/1998 | Hoffman et al. | 6,090,096 A | 7/2000 | St. Goar et al. |
| 5,743,267 A | 4/1998 | Nikolic et al. | 6,102,678 A | 8/2000 | Peciat et al. |
| 5,749,369 A | 5/1998 | Rabinovich et al. | 6,102,856 A | 8/2000 | Groff et al. |
| 5,749,909 A | 5/1998 | Schroeppel et al. | 6,102,922 A | 8/2000 | Jakobsson et al. |
| 5,755,687 A | 5/1998 | Donion | 6,106,477 A | 8/2000 | Meisel et al. |
| 5,755,748 A | 5/1998 | Borza et al. | 6,106,551 A | 8/2000 | Crossett et al. |
| 5,765,568 A | 6/1998 | Sweezer, Jr. et al. | 6,110,145 A | 8/2000 | Macoviak |
| 5,769,812 A | 6/1998 | Stevens et al. | 6,113,553 A | 9/2000 | Chubbuck |
| 5,771,903 A | 6/1998 | Jakobsson | 6,131,664 A | 10/2000 | Sonnier |
| 5,782,774 A | 7/1998 | Shmulewitz | 6,135,945 A | 10/2000 | Sultan |
| 5,787,520 A | 8/1998 | Dunbar | 6,152,885 A | 11/2000 | Taepke |
| 5,791,344 A | 8/1998 | Schulman et al. | 6,158,965 A | 12/2000 | Butterfield et al. |
| 5,792,094 A | 8/1998 | Stevens et al. | 6,159,156 A | 12/2000 | Van Bockel et al. |
| 5,792,179 A | 8/1998 | Sideris | 6,162,180 A | 12/2000 | Miesel et al. |
| 5,795,325 A | 8/1998 | Valley et al. | 6,162,245 A | 12/2000 | Jayaraman et al. |
| 5,796,827 A | 8/1998 | Coppersmith et al. | 6,168,614 B1 | 1/2001 | Andersen et al. |
| 5,797,403 A | 8/1998 | DiLorenzo | 6,171,252 B1 | 1/2001 | Roberts |
| 5,800,375 A | 9/1998 | Sweezer et al. | 6,210,347 B1 | 4/2001 | Forsell |
| 5,803,917 A | 9/1998 | Butter field et al. | 6,216,028 B1 | 4/2001 | Haynor et al. |
| 5,807,265 A | 9/1998 | Itoigawa et al. | 6,234,745 B1 | 5/2001 | Pugh et al. |
| 5,807,336 A | 9/1998 | Russo et al. | 6,240,316 B1 | 5/2001 | Richmond et al. |
| 5,810,015 A | 9/1998 | Flaherty | 6,240,318 B1 | 5/2001 | Phillips |
| 5,810,757 A | 9/1998 | Sweezer, Jr. et al. | 6,245,102 B1 | 6/2001 | Jayaraman |
| 5,810,841 A | 9/1998 | McNeirney et al. | 6,248,080 B1 | 6/2001 | Miesel et al. |
| 5,814,016 A | 9/1998 | Valley et al. | 6,251,093 B1 | 6/2001 | Valley et al. |
| 5,817,093 A | 10/1998 | Williamson, IV et al. | 6,269,819 B1 | 8/2001 | Oz et al. |
| 5,833,603 A | 11/1998 | Kovacs et al. | 6,277,078 B1 | 8/2001 | Porat et al. |
| 5,836,300 A | 11/1998 | Mault | 6,285,897 B1 | 9/2001 | Kilcoyne et al. |
| 5,836,886 A | 11/1998 | Itoigawa et al. | 6,292,697 B1 | 9/2001 | Roberts |
| 5,840,081 A | 11/1998 | Anderson et al. | 6,305,381 B1 | 10/2001 | Weijand et al. |
| 5,849,225 A | 12/1998 | Ebina et al. | 6,309,350 B1 | 10/2001 | Van Tassel et al. |
| 5,855,597 A | 1/1999 | Jayaraman et al. | 6,315,769 B1 | 11/2001 | Peer et al. |
| 5,855,601 A | 1/1999 | Bessler et al. | 6,319,208 B1 | 11/2001 | Abita et al. |
| 5,860,938 A | 1/1999 | LaFontaine et al. | 6,328,699 B1 | 12/2001 | Eigler et al. |
| 5,861,018 A | 1/1999 | Feierbach | 6,338,735 B1 | 1/2002 | Stevens |
| 5,863,366 A | 1/1999 | Snow | 6,357,438 B1 | 3/2002 | Hansen |
| 5,868,702 A | 2/1999 | Stevens et al. | 6,360,122 B1 | 3/2002 | Fischell et al. |
| 5,873,837 A | 2/1999 | Lieber et al. | 6,360,822 B1 | 3/2002 | Robertson et al. |
| 5,875,953 A | 3/1999 | Shioya et al. | 6,366,799 B1 | 4/2002 | Acker et al. |
| 5,879,499 A | 3/1999 | Corvi | 6,366,817 B1 | 4/2002 | Kung |
| 5,881,919 A | 3/1999 | Womac et al. | 6,379,308 B1 | 4/2002 | Brockway et al. |
| 5,885,238 A | 3/1999 | Stevens et al. | 6,379,380 B1 | 4/2002 | Satz |
| 5,887,475 A | 3/1999 | Muldner | 6,398,752 B1 | 6/2002 | Sweezer, Jr. et al. |
| 5,899,927 A | 5/1999 | Ecker et al. | 6,409,674 B1 | 6/2002 | Brockway et al. |
| 5,916,179 A | 6/1999 | Sharrock | 6,416,291 B1 | 7/2002 | Butterfield et al. |
| 5,916,237 A | 6/1999 | Schu | 6,423,031 B1 | 7/2002 | Donlon |
| 5,928,182 A | 7/1999 | Kraus et al. | 6,430,444 B1 | 8/2002 | Borza et al. |
| 5,935,078 A | 8/1999 | Feierbach | 6,431,175 B1 | 8/2002 | Penner et al. |
| 5,935,083 A | 8/1999 | Williams | 6,432,040 B1 | 8/2002 | Meah |
| 5,938,669 A | 8/1999 | Klaiber et al. | 6,443,887 B1 | 9/2002 | Derus et al. |
| 5,951,487 A | 9/1999 | Brehmeier-Flick et al. | 6,443,893 B1 | 9/2002 | Schnakenberg et al. |

| | | |
|---|---|---|
| 6,450,173 B1 | 9/2002 | Forsell |
| 6,450,543 B1 | 9/2002 | Fukano et al. |
| 6,450,946 B1 | 9/2002 | Forsell |
| 6,453,907 B1 | 9/2002 | Forsell et al. |
| 6,454,698 B1 | 9/2002 | Forsell et al. |
| 6,454,700 B1 | 9/2002 | Forsell |
| 6,454,701 B1 | 9/2002 | Forsell |
| 6,460,543 B1 | 10/2002 | Forsell et al. |
| 6,461,292 B1 | 10/2002 | Forsell et al. |
| 6,461,293 B1 | 10/2002 | Forsell |
| 6,463,329 B1 | 10/2002 | Goedeke |
| 6,463,935 B1 | 10/2002 | Forsell |
| 6,464,628 B1 | 10/2002 | Forsell |
| 6,470,212 B1 | 10/2002 | Weijand et al. |
| 6,470,213 B1 | 10/2002 | Alley |
| 6,470,892 B1 | 10/2002 | Forsell |
| 6,471,635 B1 | 10/2002 | Forsell |
| 6,475,136 B1 | 11/2002 | Forsell |
| 6,475,170 B1 | 11/2002 | Doron et al. |
| 6,481,292 B1 | 11/2002 | Reich |
| 6,482,145 B1 | 11/2002 | Forsell |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,503,208 B1 | 1/2003 | Skovlund et al. |
| 6,504,286 B1 | 1/2003 | Porat et al. |
| 6,505,062 B1 | 1/2003 | Ritter et al. |
| 6,511,490 B2 | 1/2003 | Robert |
| 6,516,062 B1 | 2/2003 | Yang et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,543,907 B2 | 4/2003 | Nishiyama et al. |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,587,709 B2 | 7/2003 | Solf et al. |
| 6,589,189 B2 | 7/2003 | Meyerson et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | Van Tassel et al. |
| 6,654,629 B2 | 11/2003 | Montegrande |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers |
| 6,689,046 B2 | 2/2004 | Sayet et al. |
| 6,690,963 B2 | 2/2004 | Ben-Haim et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,757,557 B1 | 6/2004 | Bladen et al. |
| 6,779,851 B2 | 8/2004 | Bouchiere |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaeft et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,143,462 B2 | 12/2006 | Hohlbein |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0023134 A1 | 1/2003 | Tracey |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0120150 A1 | 6/2003 | Govari |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2003/0225371 A1 | 12/2003 | Hadzic et al. |
| 2004/0014456 A1 | 1/2004 | Vnnen |
| 2004/0016874 A1 | 1/2004 | Rao et al. |
| 2004/0039256 A1 | 2/2004 | Kawatahara et al. |
| 2004/0054351 A1 | 3/2004 | Deniega et al. |
| 2004/0054352 A1 | 3/2004 | Adams et al. |
| 2004/0055610 A1 | 3/2004 | Forsell |
| 2004/0064030 A1 | 4/2004 | Forsell |
| 2004/0082867 A1 | 4/2004 | Esch et al. |
| 2004/0082904 A1 | 4/2004 | Houde et al. |
| 2004/0113790 A1 | 6/2004 | Hamel et al. |
| 2004/0133092 A1 | 7/2004 | Kain |
| 2004/0143212 A1 | 7/2004 | Trombley et al. |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0193045 A1 | 9/2004 | Scarborough et al. |
| 2004/0215159 A1 | 10/2004 | Forsell |
| 2004/0243148 A1 | 12/2004 | Wasielewski |
| 2004/0254537 A1 | 12/2004 | Conlon et al. |

| | | |
|---|---|---|
| 2005/0004516 A1 | 1/2005 | Vanney |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0027998 A1 | 2/2005 | Teglia et al. |
| 2005/0038328 A1 | 2/2005 | Stoehrer et al. |
| 2005/0061079 A1 | 3/2005 | Schulman |
| 2005/0065450 A1 | 3/2005 | Stuebe et al. |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0203360 A1 | 9/2005 | Brauker et al. |
| 2005/0240144 A1 | 10/2005 | Wassermann et al. |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hasslet et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0089619 A1 | 4/2006 | Ginggen |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0118793 A1 | 6/2006 | Yang et al. |
| 2006/0122285 A1 | 6/2006 | Fallon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149161 A1 | 7/2006 | Wilson et al. |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |
| 2008/0172072 A1 | 7/2008 | Pool et al. |
| 2008/0250340 A1 | 10/2008 | Dlugos et al. |
| 2008/0250341 A1 | 10/2008 | Dlugos et al. |
| 2009/0005703 A1 | 1/2009 | Fasciano |
| 2010/0179488 A1 * | 7/2010 | Spiegel et al. ............ 604/240 |

FOREIGN PATENT DOCUMENTS

| | | |
|---|---|---|
| CA | 1059035 | 7/1979 |
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1119469 | 3/1982 |
| CN | 1059035 | 2/1992 |
| CN | 1241003 | 1/2000 |
| DE | 9416395 | 12/1994 |
| DE | 10156494 | 6/2003 |
| EA | 4581 | 6/2004 |
| EP | 0417171 | 3/1991 |
| EP | 0508141 | 10/1992 |
| EP | 0568730 | 11/1993 |
| EP | 0605302 | 7/1994 |
| EP | 0 654 232 | 5/1995 |
| EP | 0660482 | 6/1995 |
| EP | 0714017 | 5/1996 |
| EP | 0769340 | 4/1997 |
| EP | 0846475 | 6/1998 |
| EP | 0848780 | 6/1998 |
| EP | 0876808 | 11/1998 |
| EP | 0888079 | 1/1999 |
| EP | 0914059 | 5/1999 |
| EP | 0981293 | 3/2000 |
| EP | 0997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1442715 | 8/2004 |

| | | |
|---|---|---|
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1600120 | 11/2005 |
| EP | 1609440 | 12/2005 |
| EP | 1649884 | 4/2006 |
| EP | 1674033 | 6/2006 |
| EP | 1 676 527 | 7/2006 |
| EP | 1704833 | 9/2006 |
| EP | 1 736 123 | 12/2006 |
| EP | 1736123 | 12/2006 |
| EP | 1799119 | 6/2007 |
| GB | 2355937 | 5/2001 |
| JP | 2006/175191 | 7/2006 |
| WO | WO 89/11244 | 11/1989 |
| WO | WO 89/11701 | 11/1989 |
| WO | WO 90/04368 | 5/1990 |
| WO | WO 95/11057 | 4/1995 |
| WO | WO 97/15351 | 5/1997 |
| WO | WO 97/33513 | 9/1997 |
| WO | WO 98/33554 | 8/1998 |
| WO | WO 98/35610 | 8/1998 |
| WO | WO 99/01063 | 1/1999 |
| WO | WO 99/18850 | 4/1999 |
| WO | WO 00/04945 | 2/2000 |
| WO | WO 00/33738 | 6/2000 |
| WO | WO 00/72899 | 12/2000 |
| WO | WO 01/04487 | 1/2001 |
| WO | WO 01/12075 | 2/2001 |
| WO | WO 01/12076 | 2/2001 |
| WO | WO 01/12077 | 2/2001 |
| WO | WO 01/12078 | 2/2001 |
| WO | WO 01/21066 | 3/2001 |
| WO | WO 01/36014 | 5/2001 |
| WO | WO 01/45485 | 6/2001 |
| WO | WO 01/45486 | 6/2001 |
| WO | WO 01/47431 | 7/2001 |
| WO | WO 01/47432 | 7/2001 |
| WO | WO 01/47433 | 7/2001 |
| WO | WO 01/47434 | 7/2001 |
| WO | WO 01/47435 | 7/2001 |
| WO | WO 01/47440 | 7/2001 |
| WO | WO 01/47575 | 7/2001 |
| WO | WO 01/48451 | 7/2001 |
| WO | WO 01/49245 | 7/2001 |
| WO | WO 01/50832 | 7/2001 |
| WO | WO 01/50833 | 7/2001 |
| WO | WO 01/54626 | 8/2001 |
| WO | WO 01/58388 | 8/2001 |
| WO | WO 01/58390 | 8/2001 |
| WO | WO 01/58391 | 8/2001 |
| WO | WO 01/58393 | 8/2001 |
| WO | WO 01/60453 | 8/2001 |
| WO | WO 01/81890 | 11/2001 |
| WO | WO 02/00118 | 1/2002 |
| WO | WO 02/15769 | 2/2002 |
| WO | WO 02/26161 | 4/2002 |
| WO | WO 02/053228 | 7/2002 |
| WO | WO 02/055126 | 7/2002 |
| WO | WO 02/058551 | 8/2002 |
| WO | WO 02/065894 | 8/2002 |
| WO | WO 02/076289 | 10/2002 |
| WO | WO 02/082984 | 10/2002 |
| WO | WO 02/089655 | 11/2002 |
| WO | WO 02/090894 | 11/2002 |
| WO | WO 02/100481 | 12/2002 |
| WO | WO 03/002192 | 1/2003 |
| WO | WO 03/002193 | 1/2003 |
| WO | WO 03/020182 | 3/2003 |
| WO | WO 03/043534 | 5/2003 |
| WO | WO 03/061467 | 7/2003 |
| WO | WO 03/061504 | 7/2003 |
| WO | WO 03/096889 | 11/2003 |
| WO | WO 2004/014245 | 2/2004 |
| WO | WO 2004/019773 | 3/2004 |
| WO | WO 2004/030541 | 4/2004 |
| WO | WO 2004/058101 | 7/2004 |
| WO | WO 2004/066879 | 8/2004 |
| WO | WO 2004/110263 | 12/2004 |
| WO | WO 2005/000206 | 1/2005 |
| WO | WO 2005/007075 | 1/2005 |
| WO | WO 2005/027998 | 3/2005 |
| WO | WO 2005/084544 | 9/2005 |
| WO | WO 2005/107583 | 11/2005 |
| WO | WO 2006/001851 | 1/2006 |
| WO | WO 2006/018927 | 2/2006 |
| WO | WO 2006/035446 | 4/2006 |
| WO | WO 2006/113187 | 10/2006 |
| WO | WO 2006/122285 | 11/2006 |
| WO | WO 2007/067206 | 6/2007 |
| WO | WO 2007/070906 | 6/2007 |
| WO | WO 2007/072452 | 6/2007 |
| WO | WO 2007/081304 | 7/2007 |
| WO | WO 2007/104356 | 9/2007 |
| WO | WO 2007/140430 | 12/2007 |
| WO | WO 2008/088949 | 7/2008 |

OTHER PUBLICATIONS

European Search Report dated Jul. 10, 2009 for Application No. 09250590.
European Search Report dated Jul. 10, 2009 for Application No. 09250600.
European Search Report dated Aug. 13, 2009 for Application No. 08251093.
International Search Report and Written Opinion dated Sep. 22, 2008 for Application No. PCT/US2008/053394.
European Search Report dated May 2, 2008 for Application No. EP 06250968.
European Examination Report dated Dec. 9, 2008 for Application No. EP 06250968.
European Search Report dated Nov. 3, 2008 for Application No. EP 08251508.
European Examination Report dated Jul. 23, 2007 for Application No. EP 06253286.
European Search Report dated Sep. 28, 2006 for Application No. EP 06253286.
European Search Report dated Feb. 10, 2009 for Application No. EP 07250915.
Abstract for JP2006/175191.
U.S. Appl. No. 12/039,014, filed Feb. 28, 2008, Dlugos, Jr. et al.
EP Search Report dated Jun. 13, 2007 for Application No. 07250931.
EP Search Report dated Jun. 18, 2007 for Application No. 07250932.
Kirchner, G., "Honeywell and Synopsys: Concept-to-Parts Solutions for Next Generation Rad-Hard ASICs," in online magazine Compiler, http://www.synopsys.com/news/pubs/compiler/artlead_redasic-apr05.html,(Apr. 2005), pp. 1-5.
Lechner, W., "In Vivo Band Manometry: a New Access to Band Adjustment," Obesity Surgery, vol. 15 (2005) pp. 1432-1436.
"Wireless in Healthcare," The FocalPoint Group, www.thefpgroup.com (2004) pp. 1-85.
EPO Search Report dated Jul. 12, 2007, for EP Application No. 07250931.8.
EPO Search Report dated Jul. 23, 2007, for EP Application No. 07250932.6.

* cited by examiner

EXTERNAL MECHANICAL PRESSURE SENSOR FOR GASTRIC BAND PRESSURE MEASUREMENTS

PRIORITY

This application is a continuation-in-part of prior co-pending U.S. Non-Provisional application Ser. No. 11/369,389, filed Mar. 7, 2006, entitled "External Pressure-Based Gastric Band Adjustment System and Method," and published as U.S. Pub. No. 2006/0211912, which is a continuation-in-part of prior co-pending U.S. Non-Provisional application Ser. No. 11/065,410, filed Feb. 24, 2005, entitled "Device for Non-Invasive Measurement of Fluid Pressure in an Adjustable Restriction Device," and published as U.S. Pub. No. 2006/0189888. The disclosure of each of those applications and publications is incorporated by reference herein.

BACKGROUND

Many devices and methods for treating obesity have been made and used, including but not limited to adjustable gastric bands. An example of such an adjustable gastric band is disclosed in U.S. Pat. No. 6,067,991, entitled "Mechanical Food Intake Restriction Device," which issued on May 30, 2000, and which is incorporated herein by reference. To the extent that an adjustable gastric band system is fluid based, those of ordinary skill in the art will appreciate that it may be advantageous to acquire data indicating the pressure of fluid in the band system. Similar advantages may be achieved with fluid-filled members implanted within the stomach cavity or elsewhere. Such pressure data may be obtained before, during, and/or after pressure adjustment, and may be useful for adjustment, diagnostic, monitoring, or other purposes. The foregoing examples are merely illustrative and not exhaustive. While a variety of techniques and devices have been used treat obesity, it is believed that no one prior to the inventors has previously made or used an invention as described in the appended claims.

BRIEF DESCRIPTION OF THE FIGURES

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
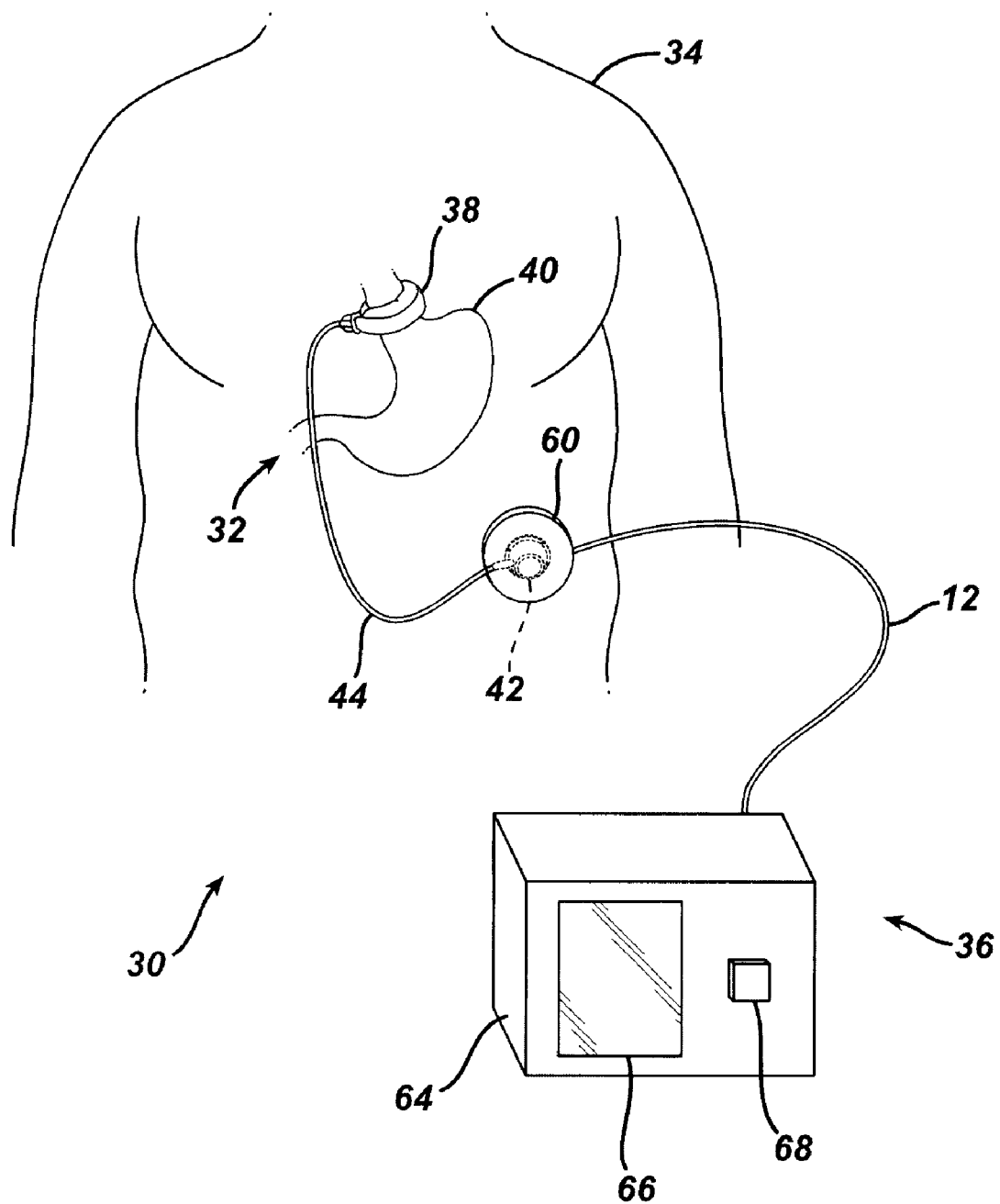
FIG. 1 is a schematic illustration of an exemplary food intake restriction system.

Referring now to the drawings in detail, wherein like numerals indicate the same elements throughout the views, FIG. 1 illustrates a food intake restriction system 30. System 30 comprises a first portion, identified generally as 32, implanted inside of a patient 34, and a second portion, identified generally as 36, located external to the patient. Implanted portion 32 comprises an adjustable gastric band 38 positioned on the upper portion of the patient's stomach 40.

Adjustable band 38 may include a cavity made of silicone rubber, or another type of biocompatible material, that inflates inwardly against stomach 40 when filled with a fluid. Alternatively, band 38 may comprise a mechanically adjustable device having a fluid cavity that experiences pressure changes with band adjustments, or a combination hydraulic/mechanical adjustable band. In the present example, an injection port 42, which will be described in greater detail below, is implanted in a body region accessible for needle injections and/or telemetry communication signals. In the embodiment shown, injection port 42 fluidly communicates with adjustable band 38 via a catheter 44. A surgeon may position and permanently implant injection port 42 inside the body of the patient in order to perform adjustments of the food intake restriction or stoma created by adjustable band 38. The surgeon, for example, may implant injection port 42 in the lateral, subcostal region of the patient's abdomen under the skin and layers of fatty tissue. The surgeon may also implant injection port 42 on the sternum of the patient. Of course, any other suitable implantation sites may be used.

Figure 2:
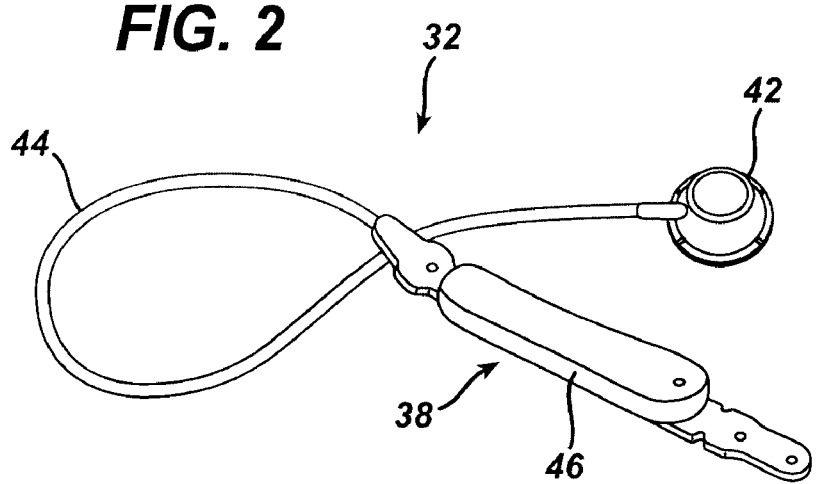
FIG. 2 is a more detailed perspective view of an exemplary implantable portion for the food intake restriction system of FIG. 1.

FIG. 2 illustrates an exemplary adjustable gastric band 38 in greater detail. In this embodiment, band 38 includes a variable volume cavity 46 that expands or contracts against the outer wall of the stomach 40 to form an adjustable stoma for controllably restricting food intake into the stomach 40. A physician may decrease the size of the stoma opening by adding fluid to variable volume cavity 46 or, alternatively, may increase the stoma size by withdrawing fluid from the cavity 46. Fluid may be added or withdrawn by inserting a needle into injection port 42. Alternatively, fluid may be transferred in a non-invasive manner between band 38 and injection port 42 using telemetry command signals. The fluid may be, but is not restricted to, a 0.9 percent saline solution.

Figure 3:
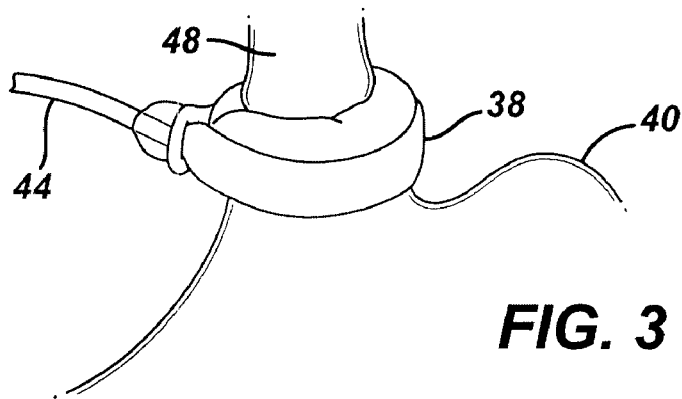
FIG. 3 is a perspective view of the adjustable gastric band of FIG. 2, showing the band positioned around the gastroesophageal junction of a patient in an exemplary use.
Figure 4:
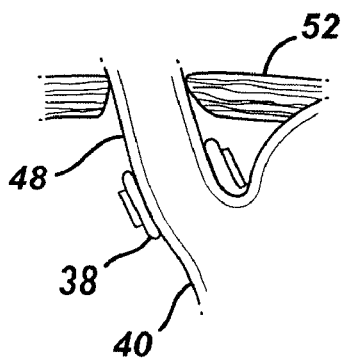
FIG. 4 is a cross-sectional view of the adjustable gastric band of FIG. 2, shown in an exemplary deflated configuration.
Figure 5:
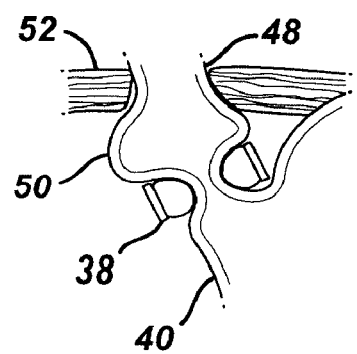
FIG. 5 is a cross-sectional view of the adjustable gastric band of FIG. 2, shown in an exemplary inflated configuration to create a food intake restriction.

FIG. 3 shows the adjustable gastric band 38 of FIG. 2 applied about the gastro-esophageal junction of a patient in an exemplary use. As shown in FIG. 3, band 38 at least substantially encloses the upper portion of stomach 40 near the junction with esophagus 48. FIG. 4 is a sectional view of band 38, showing the band 38 in a deflated configuration. In this view, band 38 contains little to no fluid, thereby maximizing the size of the stoma opening into stomach 40. FIG. 5 is a cross-sectional view of band 38 and stomach 40, similar to FIG. 4, showing band 38 in an inflated, fluid-filled configuration. In this view, the pressure of band 38 against stomach 40 is increased due to the fluid within band 38, thereby decreasing the stoma opening to create a food intake restriction. FIG. 5 also schematically illustrates the dilation of esophagus 48 above band 38 to form an upper pouch 50 beneath the diaphragm muscle 52 of the patient.

Returning now to FIG. 1, external portion 36 of food restriction system 30 comprises a pressure-reading device 60 electrically connected (in this embodiment, via an electrical cable assembly 62) to a control box 64. Control box 64 includes a display 66, one or more control switches 68, and an external control module, which will be explained in further detail below. Control box 64 may be configured for use, for example, in a physician's office or examination room. Some ways to mount control box 64 include placement upon a desktop, attachment to an examination table, or hanging on a portable stand. Control box 64 may also be configured for carrying in the physician's lab coat pocket, holding by hand, or placing upon the examination table or the reclining patient. Electrical cable assembly 62 may be detachably connected to control box 64 or pressure-reading device 60 to facilitate cleaning, maintenance, usage, and storage of external portion 36 of system 30.

Pressure-reading device 60 may non-invasively measure the pressure of the fluid within implanted portion 32 even when injection port 42 is implanted beneath thick (e.g., at least over 10 centimeters) subcutaneous fat tissue. For instance, implanted portion 32 may comprise one or more pressure sensors, and pressure-reading device 60 may be configured to obtain pressure data from implanted portion 32 via telemetry or other means. To the extent that implanted portion 32 requires power from an external source, pressure-reading device 60 or some other component, may be further configured to provide transcutaneous energy transfer (TET) to implanted portion. In the present example, a physician may hold pressure-reading device 60 against the patient's skin near the location of injection port 42 in the patient and observe the pressure reading on display 66 of control box 64. Pressure-reading device 60 may also be removably attached to the patient 34, such as during a prolonged examination, using straps, adhesives, and other well-known methods. Pressure-reading device 60 operates through conventional cloth or paper surgical drapes, and may also include a disposal cover (not shown) that may be replaced for each patient.

Figure 6:
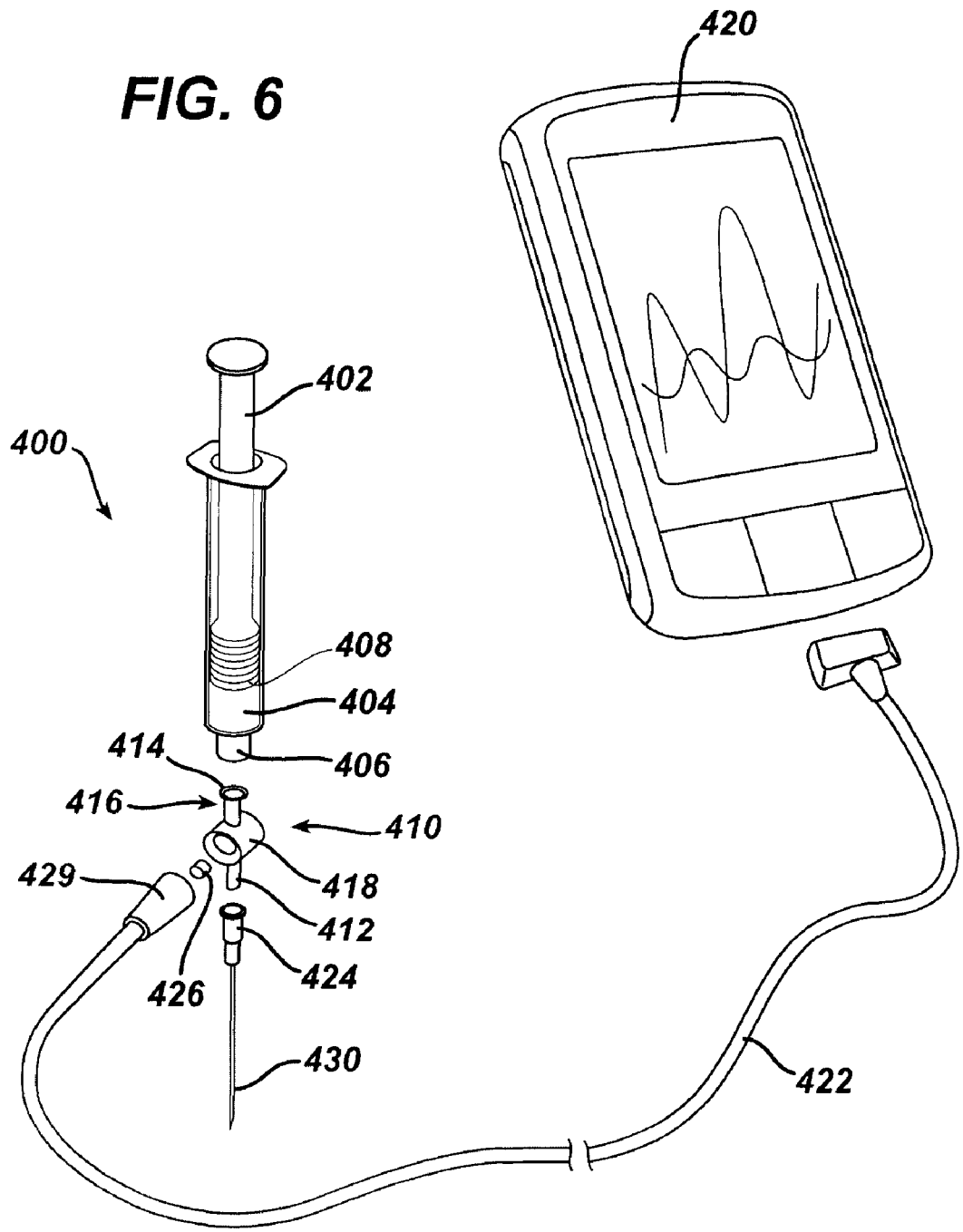
FIG. 6 is a perspective exploded view of an exemplary syringe system with pressure sensor and display device.
Figure 7:
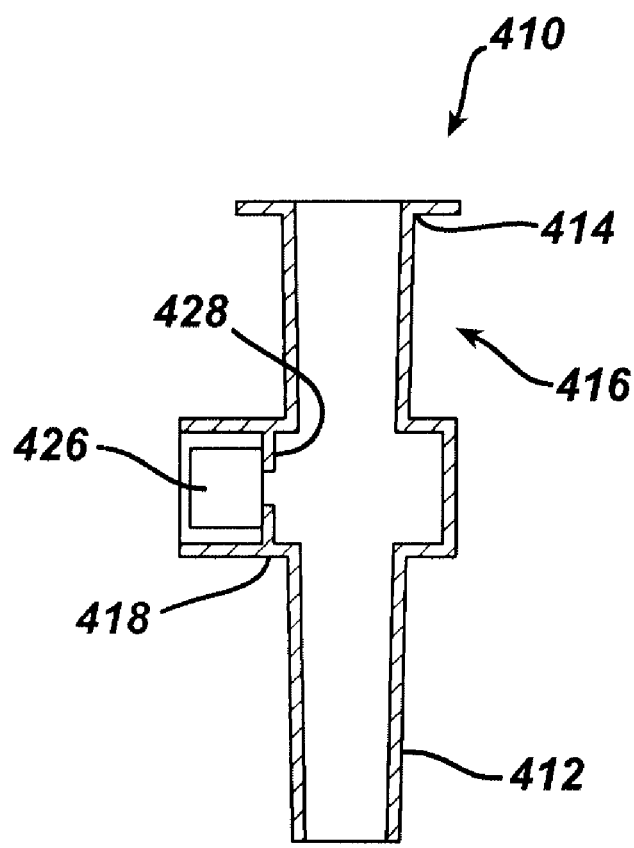
FIG. 7 is a cross-sectional view of a pressure sensing portion of the syringe system of FIG. 6.

While the above embodiments contemplate a pressure sensor being implanted within a patient 34, it will be appreciated that pressure sensors and other sensors may be provided external to a patient 34. For instance, another embodiment is shown in FIGS. 6-7, which depicts an exemplary syringe 400 and a display device 420 in communication via a cable 422. Syringe 400 comprises a plunger 402, a barrel 404, a pressure sensing component 410, and a needle 430. In the present example, plunger 402, barrel 404, and needle 430 are conventional components. Accordingly, barrel 404 has a male luer lock portion 406; and needle 430 has a female luer lock portion 424. Plunger 402 has a piston 408 configured to sealingly engage with barrel 404. In one version, needle 430 comprises a Huber needle. Of course, any of these components, among others, may be varied.

Cable 422 has a boot portion 429, which is configured to selectively attach to pressure sensing component 410. Boot portion 429 further comprises a feature (not shown) that is operable to electrically engage with pressure sensor 426, and thereby communicate pressure readings obtained by pressure sensor 426 along cable 422. Such a feature may comprise one or more terminals (not shown) or any other feature(s). In another embodiment, pressure sensing component 410 is fixedly secured to boot portion 429 and cable 422. Other suitable configurations will be apparent to those of ordinary skill in the art.

In the present example, pressure sensing component 410 comprises a male luer lock portion 412, a female luer lock portion 414, a vertical cylindraceous portion 416, a horizontal cylindraceous portion 418, and a pressure sensor 426. Male luer lock portion 412 of pressure sensing component 410 is configured to engage with female luer lock portion 424 of needle 430; while female luer lock portion 414 of pressure sensing component 410 is configured to engage with male luer lock portion 406 of barrel 404. Accordingly, it will be appreciated that pressure sensing component 410 may be retrofitted to a variety of existing syringes. Alternatively, a syringe 400 may be constructed having a pressure sensing component 410 or similar feature integrally formed within.

As shown, pressure sensor 426 is positioned within horizontal cylindraceous portion 418, adjacent to an annular flange 428. In one example, pressure sensor 426 is sealingly secured to annular flange 428. In this example, boot portion 429 comprises one or more electrodes (not shown) or similar features configured to communicate with and/or receive communications from pressure sensor 426 upon engagement of boot portion 429 with pressure sensing component 410. In another example, pressure sensor 426 is fixed within boot portion 429, and may be positioned adjacent to annular flange 428 upon engagement of boot portion 429 with pressure sensing portion 410. Alternatively, any other suitable configuration may be used.

Pressure sensor 426 may be constructed in accordance with any of the pressure sensors described above. Alternatively, pressure sensor 426 may comprise any off-the-shelf pressure sensor suitable for use, or any other type of pressure sensor. In the present example, when syringe 400 is assembled, vertical cylindraceous portion 416 provides a sealed conduit for fluid communication from barrel 404 to needle 430. Vertical cylindraceous portion 416 is further in fluid communication with horizontal cylindraceous portion 418; as is pressure sensor 426. Accordingly, it will be appreciated that pressure sensor 426 may be operable to sense pressure of fluid within syringe 400. It will also be appreciated that pressure sensed by pressure sensor 426 may be communicated to display device 420 via cable 422, and displayed thereon in any suitable format.

In one exemplary use, needle 430 is inserted into patient 34 to reach a septum of an injection port 42. Any suitable port may be used, including but not limited to a port 42 lacking a pressure sensor. Upon such insertion in the present example, needle 430 may be placed in fluid communication with implanted portion 32, such that the pressure of the fluid in implanted portion 32 and the fluid in syringe 400 may be substantially equalized. It will therefore be appreciated that pressure sensed by pressure sensor 426 may be indicative of the pressure of fluid within implanted portion 32. Such pressure information may be particularly useful during a process of adjusting pressure within implanted portion 32 via addition of fluid to implanted portion 32 with syringe 400 or via withdrawal of fluid from implanted portion 32 with syringe 400. In particular, syringe 400 may permit simultaneous adjustment and reading of fluid pressure.

For instance, a user may first insert needle 430 into patient 34 to reach the septum of an injection port 42. Upon pressure equalization, the user may then read the initial pressure via display device 420. It will be appreciated that pressure equalization may be determined by a pressure reading remaining substantially constant. The user may then add or withdraw fluid to or from implanted portion 32 using syringe 400, watching for changes in pressure indicated via display device 420. Because no valve or other mechanism is necessarily required to switch syringe 400 between a pressure sensing mode and an add/withdrawal mode, such pressure readings may be obtained as the user is adding or withdrawing fluid to or from implanted portion 32. Accordingly, pressure sensing component 410 and pressure sensor 426 may be considered substantially in-line with the other syringe 400 components. As used herein, the phrase "substantially in-line" shall be read to imply that fluid may be added or withdrawn with syringe 400 substantially contemporaneously with pressure sensing by pressure sensor 426; and that manipulation of a valve or other mechanism is not required to switch between an add/withdrawal mode of syringe 400 and a pressure sensing mode of syringe 400. However, the phrase "substantially in-line" shall not be read to require that a straight line must be able to intersect pressure sensor 426 and all other components of syringe 400.

Pressure readings may thus be obtained in approximately real-time, as the pressure is adjusted by the user with syringe 400. To the extent that there is a delay between the user's manipulation of syringe 400 and the time the pressure equalizes among syringe 400 and implanted portion 32, the user may simply wait until the pressure reading indicated by display device 420 becomes substantially constant. Other suitable uses for syringe 400 and display device 420 will be apparent to those of ordinary skill in the art.

Figure 8:
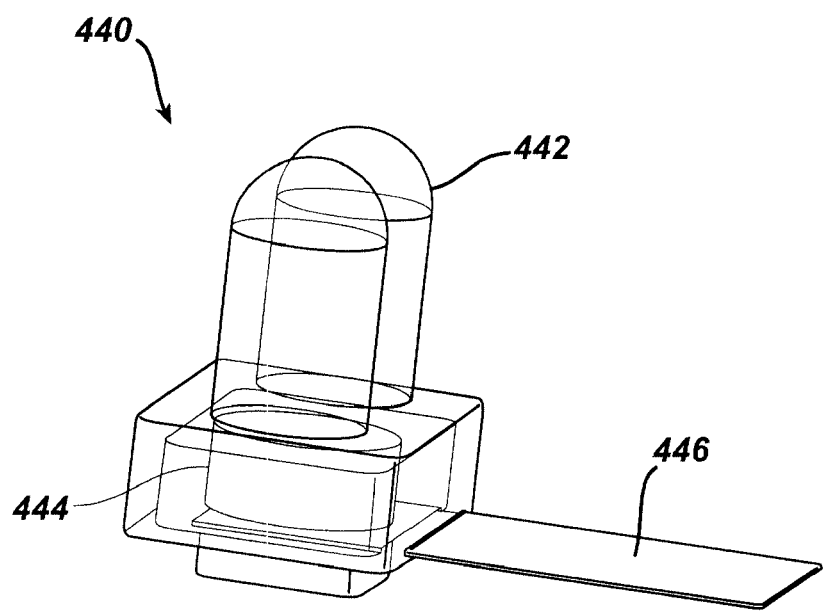
FIG. 8 is a perspective view of an exemplary infrared communicator suitable for use with the syringe system of FIG. 6.

FIG. 8 depicts an exemplary substitute for cable 422. In this variation, cable 422 of the syringe 400 version shown in FIGS. 6-7 is substituted with a wireless infrared communicator 440. Infrared communicator 440 comprises a pair of LED's 442, a battery 444, and a pull-tab 446. Infrared communicator 440 is securable to pressure sensing component 410, and is in communication with pressure sensor 426. In one embodiment, pressure sensor 426 is housed within infrared communicator 440, and is configured to be exposed to the pressure of fluid within pressure sensing component 410 when coupled with pressure sensing component 410. For instance, such pressure exposure may be provided by having pressure sensor 426 in direct contact with fluid in pressure sensing component 410. Alternatively, infrared communicator 440 and/or pressure sensing component 410 may comprise a diaphragm or other member operable to communicate pressure forces to pressure sensor 426 positioned between pressure sensor 426 and fluid in pressure sensing component 410. In yet another embodiment, pressure sensor 426 is a component of pressure sensing component 410, and infrared communicator 440 is configured to receive pressure data obtained from pressure sensor 426 when coupled with pressure sensing component 410. Still other suitable configurations will be apparent to those of ordinary skill in the art.

Infrared communicator 440 of the present example is operable to communicate pressure data obtained from pressure sensor 426 via LED's 442 in infrared light. Accordingly, it will be appreciated that display device 420 may be modified to include an infrared sensor (not shown) operable to receive such communications. Battery 444 may be used to provide power to infrared communicator 440. Pull-tab 446 may be initially positioned between battery 444 and a terminal to preserve the life of battery 444 before a first use. The user may thus remove pull-tab 446 before the first use. Alternatively, infrared communicator 440 may comprise a switch or other mechanism for selectively activating battery 444. Other variations will be apparent to those of ordinary skill in the art. In addition, it will be appreciated that the wireless nature of infrared communicator 440 or other communication devices described herein may provide a degree of patient isolation, other results, or no appreciable results. It will also be appreciated that this variation of syringe 400 may be used in a manner similar to any of the other variations of syringe 400, as described above.

Figure 9:
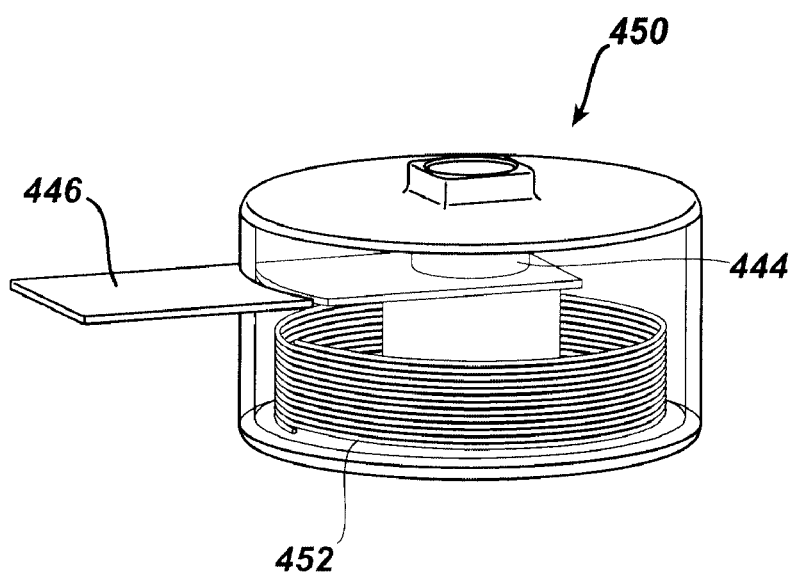
FIG. 9 is a perspective view of an exemplary RF communicator suitable for use with the syringe system of FIG. 6.

FIG. 9 shows yet another exemplary substitute for cable 422. In this variation, cable 422 of the syringe 400 version shown in FIGS. 6-7 is substituted with a wireless radio frequency (RF) communicator 450. RF communicator 450 comprises an RF coil 452, a battery 444, and a pull-tab 446. RF communicator 450 is securable to pressure sensing component 410, and is in communication with pressure sensor 426. As noted above with respect to infrared communicator 440, pressure sensor 426 may reside within RF communicator 450 or within pressure sensing component 410. other suitable configurations will be apparent to those of ordinary skill in the art.

RF communicator 450 of the present example is operable to communicate pressure data obtained from pressure sensor 426 via RF coil 452 as an RF signal. Accordingly, it will be appreciated that display device 420 may be modified to include an RF signal receiver (not shown) operable to receive such communications. Battery 444 may be used to provide power to RF communicator 450. Pull-tab 446 may be initially positioned between battery 444 and a terminal to preserve the life of battery 444 before a first use. The user may thus remove pull-tab 446 before the first use. Alternatively, RF communicator 450 may comprise a switch or other mechanism for selectively activating battery 444. Other variations will be apparent to those of ordinary skill in the art. It will also be appreciated that this variation of syringe 400 may be used in a manner similar to any of the other variations of syringe 400, as described above.

Figure 10:
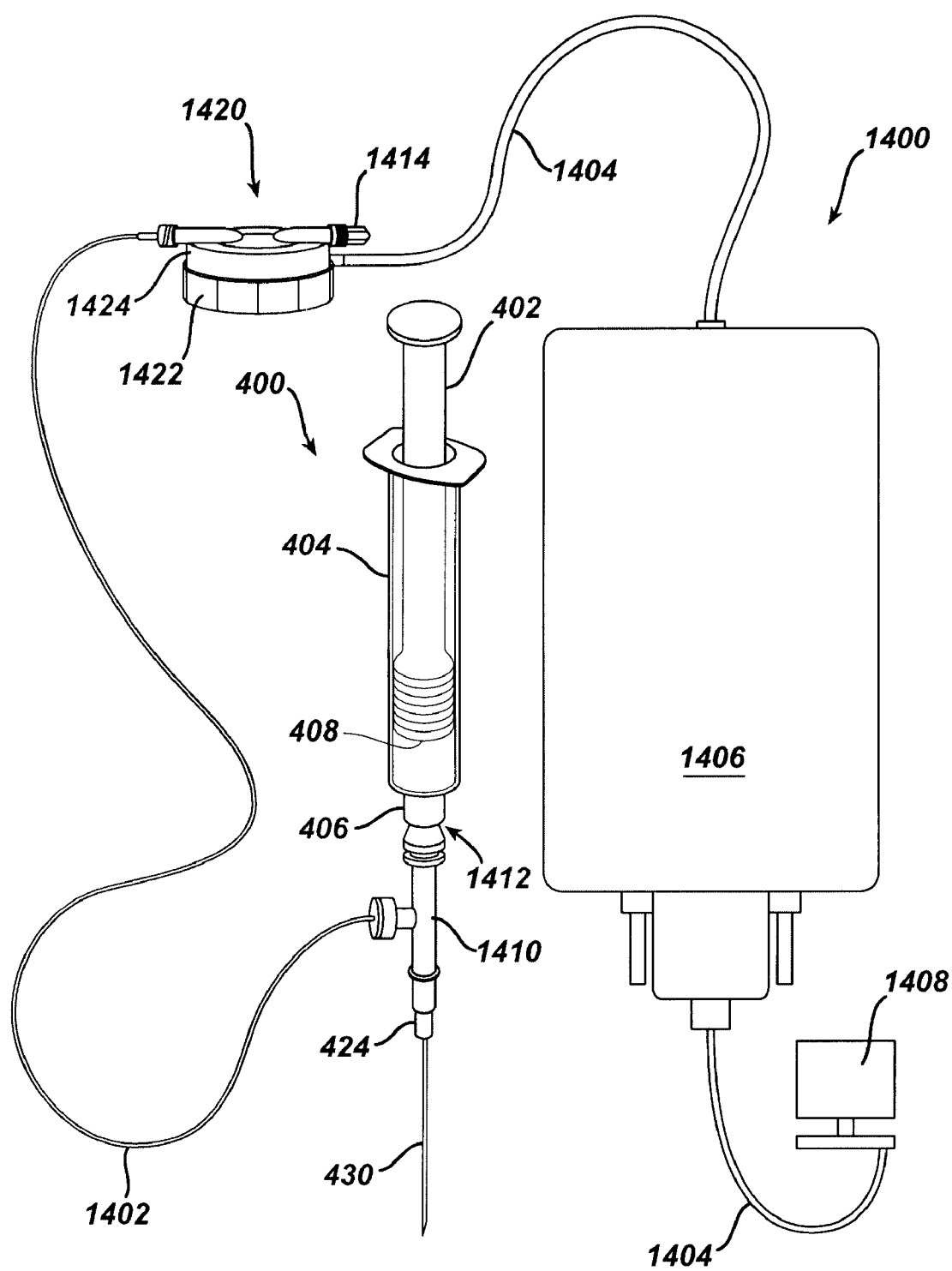
FIG. 10 is a schematic view of an alternative exemplary pressure sensing syringe system.

FIG. 10 shows another exemplary pressure sensing syringe system 1400. In this example, syringe system 1400 comprises a syringe 400, tubing 1402, a pressure sensing portion 1420, cables 1404, an interface component 1406, and a display device 1408. Syringe 400 comprises "T"-joint 1410 having a two-way leur activated valve 1412. "T"-joint 1410 is in fluid communication with needle 430 and tubing 1402. Two-way luer activated valve 1412 is configured such that it opens when "T"-joint 1410 is coupled with male luer lock portion 406 of syringe 400. Of course, a "T"-joint 1410 or other device may be provided without a two-way luer activated valve 1412. It will also be appreciated that pressure sensing component 410 described above may also have a two-way luer activated valve (e.g., at female luer lock portion 414). In the present example, when "T"-joint 1410 is coupled with syringe 400, tubing 1402 is operable to communicate the pressure of fluid within syringe 400 to pressure sensing portion 1420. It will be appreciated that "T"-joint may be secured to a variety of existing syringes 400 and needles 430. To the extent that a two-way luer activated valve 1412 or similar device is used (e.g., in "T"-joint 1410, in pressure sensing component 410, etc.), barrel 404 may be removed after pressure is adjusted without affecting fluid pressure in components "downstream" of two-way luer activated valve 1412. By way of example only, it may be desirable to adjust pressure using syringe 400, then remove barrel 404 from two-way luer activated valve 1412, then have patient 34 stand upright, then obtain subsequent pressure measurements. Removal of barrel 404 and/or other uses for two-way luer activated valve 1412 may also be desirable in a number of other situations.

Figure 11:
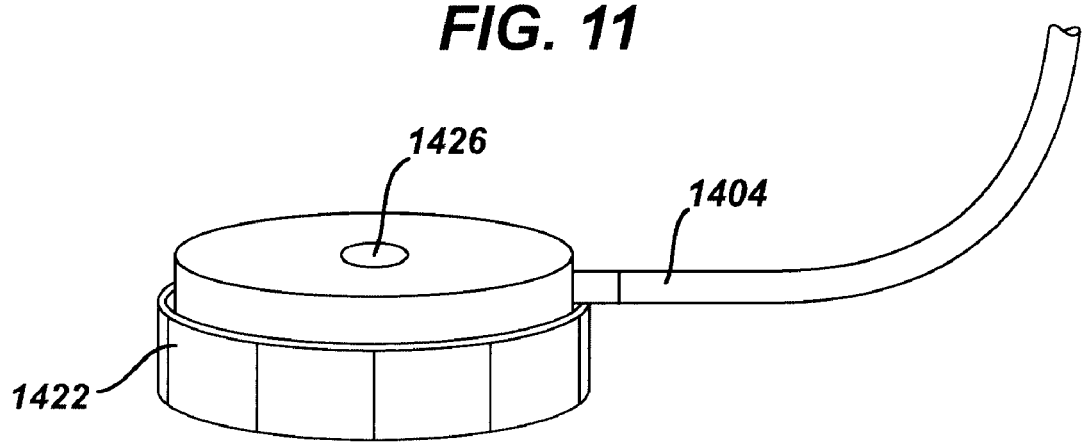
FIG. 11 is a perspective view of a reusable sensor portion of the pressure sensing syringe system of FIG. 10.
Figure 12:
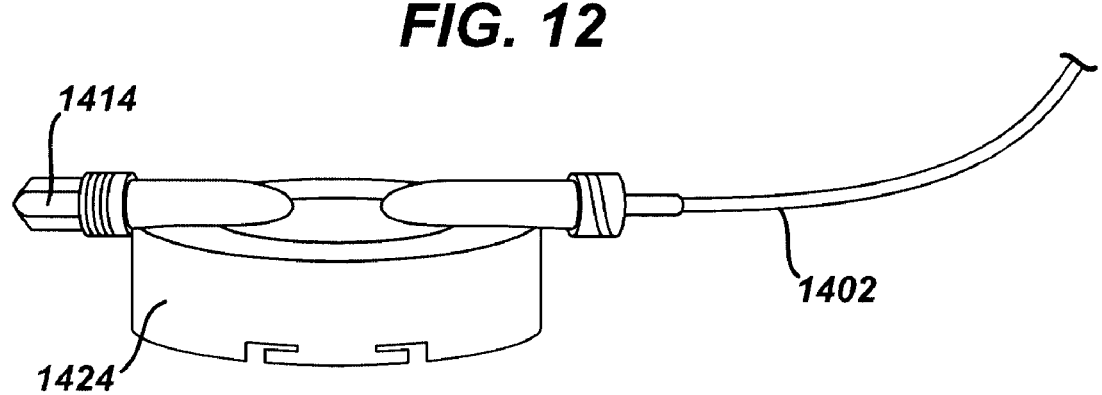
FIG. 12 is a partial perspective view of a disposable cap portion of the pressure sensing syringe system of FIG. 10.

As shown in FIGS. 10-12, pressure sensing portion 1420 comprises a reusable sensor portion 1422 and a disposable cap portion 1424. Reusable sensor portion 1422 and disposable cap portion 1424 are configured to selectively engage one another. When coupled with reusable sensor portion 1422, disposable cap portion 1424 is in fluid communication with reusable sensor portion 1422, such that pressure of fluid within tubing 1402 may be communicated to reusable sensor portion 1422 via disposable cap portion 1424. In one embodiment, disposable cap portion 1424 comprises the pressure dome described in U.S. Pat. No. 6,725,726, the disclosure of which is incorporated by reference herein. Reusable sensor portion 1422 comprises a pressure port 1426, which is configured to receive such fluid pressure communications from disposable cap portion 1424. For instance, pressure port 1426 may comprise a diaphragm or other structure suited for receiving fluid pressure communications. Reusable sensor portion 1422 further comprises a pressure sensor (not shown), such as a transducer, which is configured to provide pressure data via cable 1404 to interface component 1406. Interface component 1406 is operable to process such pressure data and communicate it to display device 1408 via cable 1404. In one embodiment, reusable sensor portion 1422 comprises a Model SP840 or SP844 sensor from MEMSCAP of Durham, N.C., though any other sensor portion 1422 component(s) may be used. Of course, interface component 1406 and display device 1408 may alternatively be integrated as a single device. Interface component 1406 and/or display device 1408 may comprise a desktop PC, a laptop computer, a personal digital assistant (PDA), a dedicated device, or any other suitable device(s).

It will be appreciated that, in order to effectively communicate the pressure of fluid in syringe 400 to reusable sensor portion 1422, it may be desirable to provide a fluid within tubing 1402. Such fluid may be provided within tubing 1402 before attempting to take pressure measurements. While the fluid within tubing 1402 may be the same type of fluid within syringe 400 (e.g. saline), any fluid may be used, including but not limited to gels, silicone fluid, saline, etc. In one embodiment, 1402 tubing is provided pre-primed, such that fluid is provided within tubing 1402 prior to use (e.g., before "T"-joint 1410 is coupled with syringe 400). In another embodiment, tubing 1402 is initially empty of fluid, and the user primes tubing 1402 with fluid before using syringe 400 to add or withdraw fluid to or from injection port 42. Accordingly, a vent cap 1414 is provided in disposable cap portion 1424 to facilitate priming of tubing 1402 with fluid by facilitating the evacuation of air from tubing 1402.

As described above, a user may use syringe 400 to add fluid to or withdraw fluid from port 42 to adjust a gastric band 38. With pressure sensing syringe system 1400 assembled as shown in FIG. 10 during such use, or when any suitable variation of pressure sensing syringe system 1400 is used, it will be appreciated that fluid pressure may be sensed, and pressure measurements may be made, as gastric band 38 pressure is adjusted. In other words, pressure may be sensed and adjusted substantially simultaneously, without the need to manipulate a stopcock valve or similar device in order to switch between solely adjusting pressure or solely sensing pressure. Alternatively, such a stopcock valve or similar device may be provided.

While reusable sensor portion 1422 and disposable cap portion 1424 are shown as being separate components, it is contemplated that these components 1422, 1424 may alternatively be unitary. Still other variations will be apparent to those of ordinary skill in the art.

Figure 13:
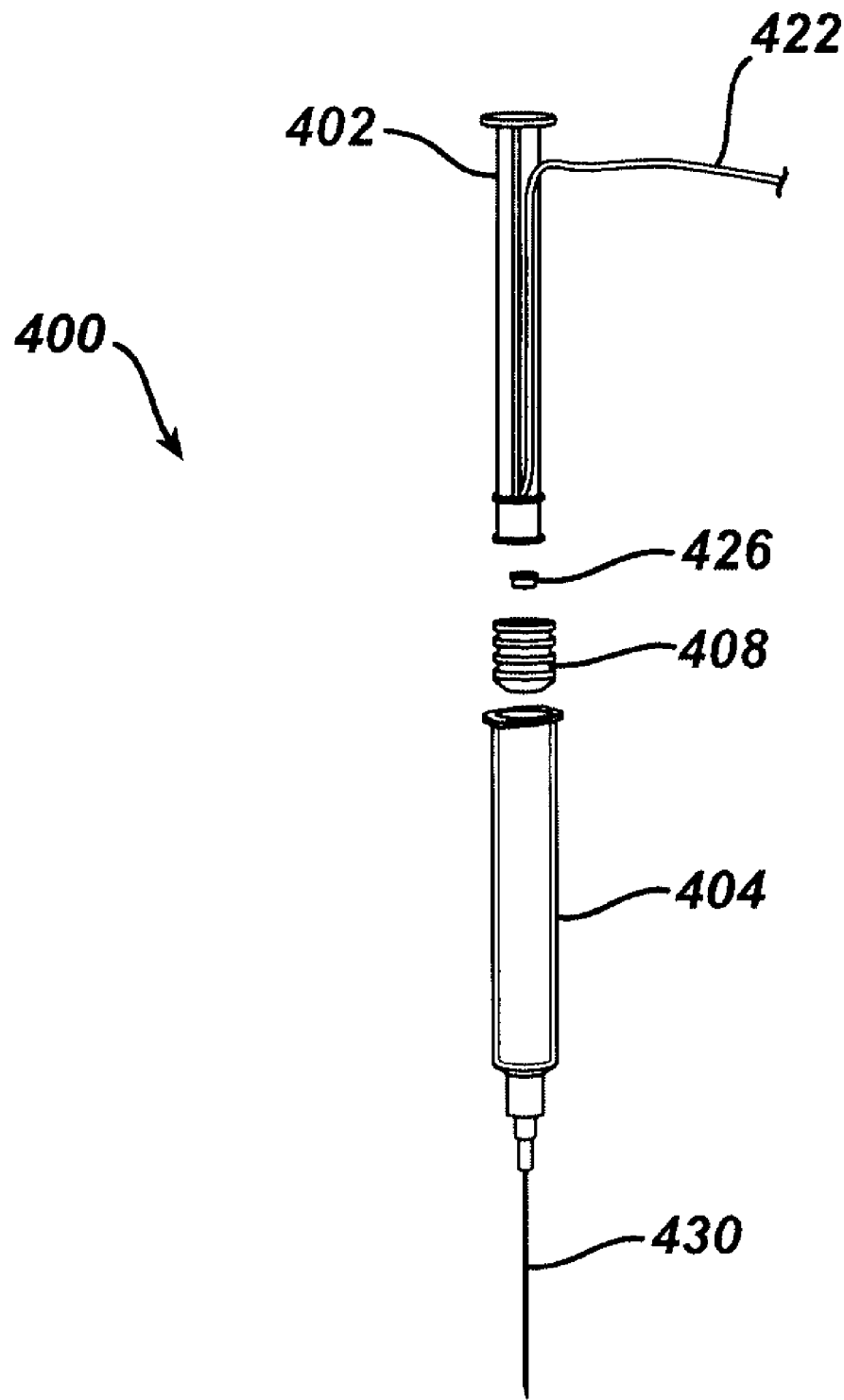
FIG. 13 is a perspective exploded view of an alternative syringe with pressure sensor.

FIG. 13 depicts a variation of syringe 400. In this variation, pressure sensor 426 is positioned between plunger 402 and piston 408, and is in communication with display device 420 via cable 422. Alternatively, pressure sensor 426 may be positioned within piston 408 or at the distal end of piston 408, such that it is in contact with fluid within barrel 404. In any of these variations, pressure sensor 426 may be configured to sense the pressure of fluid within barrel 404, and hence, the pressure of fluid within implanted portion 32 when needle 430 is placed in fluid communication with implanted portion 32. As with embodiments described above, such pressure measurements may be communicated to the user via display device 420 as the user is adding fluid to or withdrawing fluid from the implanted portion 32 via syringe 400 in approximately real-time.

The foregoing describes but a few examples of suitable locations for a pressure sensor external to a patient 34. Several other suitable locations exist, including but not limited to in barrel 404 (e.g., adjacent to male luer lock portion 406), in needle 430 (e.g., adjacent to female luer lock portion 424), or in any other suitable location. Similarly, just as syringe 400 may be varied, so may display device 420. For instance, while display device 420 of the present example is dedicated for use with pressure sensor 426, display device 420 may be any other device. By way of example only, display device 350 shown in FIG. 27 may be configured to receive communications from pressure sensor 426. Alternatively, pressure sensor 426 may be configured to communicate with a desktop PC, laptop computer, personal digital assistant (PDA), or any other device. Other variations of syringe 400 and display device 420 will be apparent to those of ordinary skill in the art, as will methods of processing pressure data. By way of example only, display device 420 or any other device may be configured to analyze pressure amplitude, the rate of change in pressure, and/or other factors to determine whether a user is using a syringe 400 that is too large, too small, or is using the syringe 400 improperly (e.g., injecting fluid too quickly, etc.), and may alert the user (e.g., visually and/or aurally) when such conditions are found.

In the present example, in any of the foregoing embodiments, it will be appreciated that and display 66 and/or display device 420 may be used to provide approximately real-time pressure measurements to a user before, during, and after the addition or withdrawal of fluid to or from implanted portion 32. For instance, a surgeon may adjust the saline content of implanted portion 32 while patient 34 swallows a fixed amount of water, and may monitor the pressure level in implanted portion via display 66 and/or display device 420 during such activities. It will be appreciated that an optimal pressure adjustment may be determined based on a variety of factors related to pressure data, including but not limited to any of the following: the original baseline pressure; the new baseline pressure; the maximum peristaltic pressure; the minimum peristaltic pressure; the length of a peristaltic contraction; the Fourier transform, Laplace transform, other transform, or other use of time/frequency domain information of a peristaltic contraction data spike; the pressure decay time constant during persistaltic contractions; the total averaged pressure decay time constant during a water swallowing period; the number of peristaltic contractions to swallow a fixed amount of water; one or more forces exerted by an implanted device and/or an anatomical structure; energy of an implanted device or of fluid therein; the fill rate of fluid into an implanted device; the volume of fluid in an implanted device; the capacity of an implanted device; the flow rate of fluid into or within an implanted device; the pressure pulse rate of fluid within an implanted device; a counted number of pressure pulses of fluid within an implanted device; one or more electrical signals communicated from tissue prior to and/or in response to adjustment of an implanted device; chemical(s) output from tissue prior to and/or in response to adjustment of an implanted device; other tissue feedback responsive to adjustment of an implanted device; or any other factors.

In one embodiment, control box 64 or display device 420 is operable to receive data indicative of the above-noted factors in any suitable fashion (e.g., from sensors, etc.), and is further operable to automatically process such factors and present the result of such processing to the user via display 66 or display device 420. For instance, control box 64 or display device 420 may be configured to determine an ideal amount of fluid to be added or withdrawn based on such processing of factors, and may simply display a message to the user such as "Add 4 cc's of fluid," "Withdraw 0.5 cc's of fluid," or the like. Such messages may be displayed in addition to or in lieu of displaying pressure measurements, changes in pressure, or other data. Other suitable processes of any of the above-noted factors or other factors, as well as ways in which results of such processes may be presented to the user, will be apparent to those of ordinary skill in the art.

As discussed above, it may be desirable to account for temperature, atmospheric pressure, and other factors when considering measurements of pressure within implanted portion 32. Accordingly, pressure-reading device 60 or any other component may receive additional data such as temperature measurements taken within implanted portion 32, and control box 64 or display device 420 may comprise logic configured to adjust pressure readings in accordance with a variety of such factors.

Figure 14:
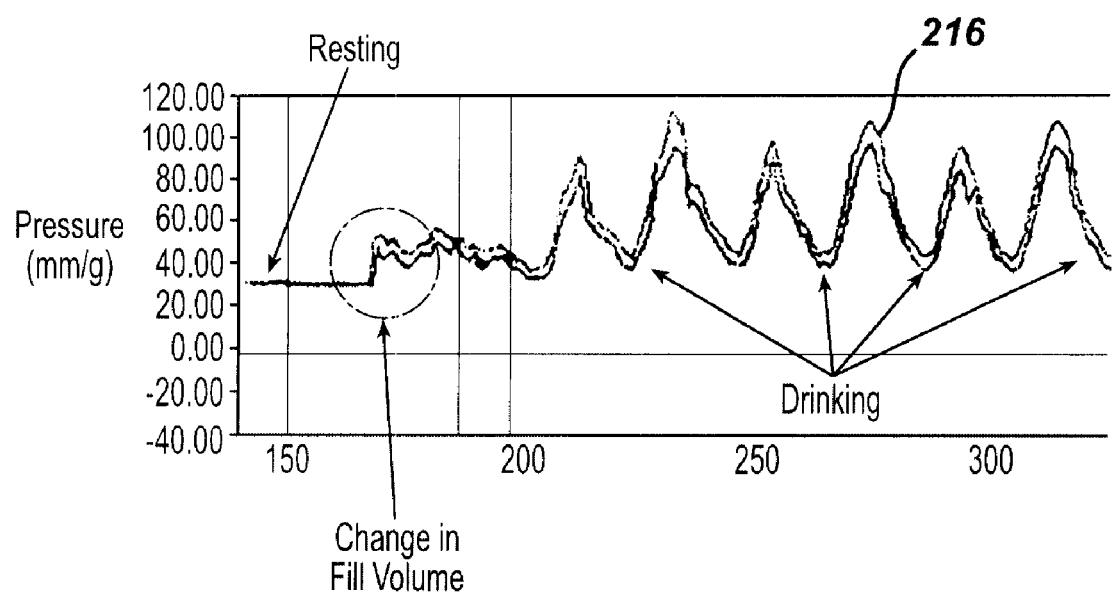
FIG. 14 is a graph indicating a pressure signal from a pressure sensing system, such as may appear on an external monitor display during interrogation by a user.

FIG. 14 is an exemplary graphical representation of a pressure signal 216 from any of the foregoing pressure sensing systems, such as may appear on display 66 or display device 420 during interrogation by a user. In one embodiment, the fluid pressure is initially measured by pressure reading device 60 or sensor 426 while the patient is stable, resulting in a steady pressure reading as shown. Next, an adjustment is applied to band 38 to decrease the stoma size. During the band adjustment, the pressure sensing system continues to measure the fluid pressure and transmit the pressure readings to control box 64 or display device 420. As seen in the graph of FIG. 14, the pressure reading rises slightly following the band adjustment. In the example shown, the patient is then asked to drink a liquid to check the accuracy of the adjustment. As the patient drinks, the pressure sensing system continues to measure the pressure spikes due to the peristaltic pressure of swallowing the liquid, and transmit the pressure readings to external module 36 for display. By measuring and visually depicting the loading of the restriction device against the peristaltic motion of the stomach both during and after an adjustment, the system of the present example provides the physician with an accurate, real-time visualization of the patient's response to the adjustment. This instantaneous, active display of recorded pressure data enables the physician to perform more accurate band adjustments. The data may be displayed over time to provide a pressure verses time history.

While several of the above embodiments comprise one or more electronic components, it will be appreciated that a pressure sensing system may alternatively comprise mechanical or other non-electronic-based pressure sensing components. For instance, several merely exemplary mechanical pressure sensing systems are depicted in FIGS. 15-25, and will be described in greater detail below. While these examples will be described as being mechanical or otherwise non-electronic-based, it will be appreciated that the following devices and components, including variations of the same, may nevertheless be modified or supplemented with a variety of electronic components, including but not limited to those electronic components described above. Furthermore, any of the devices and components described above may be modified or supplemented with a variety of mechanical components, including but not limited to the mechanical components described below.

Figure 15:
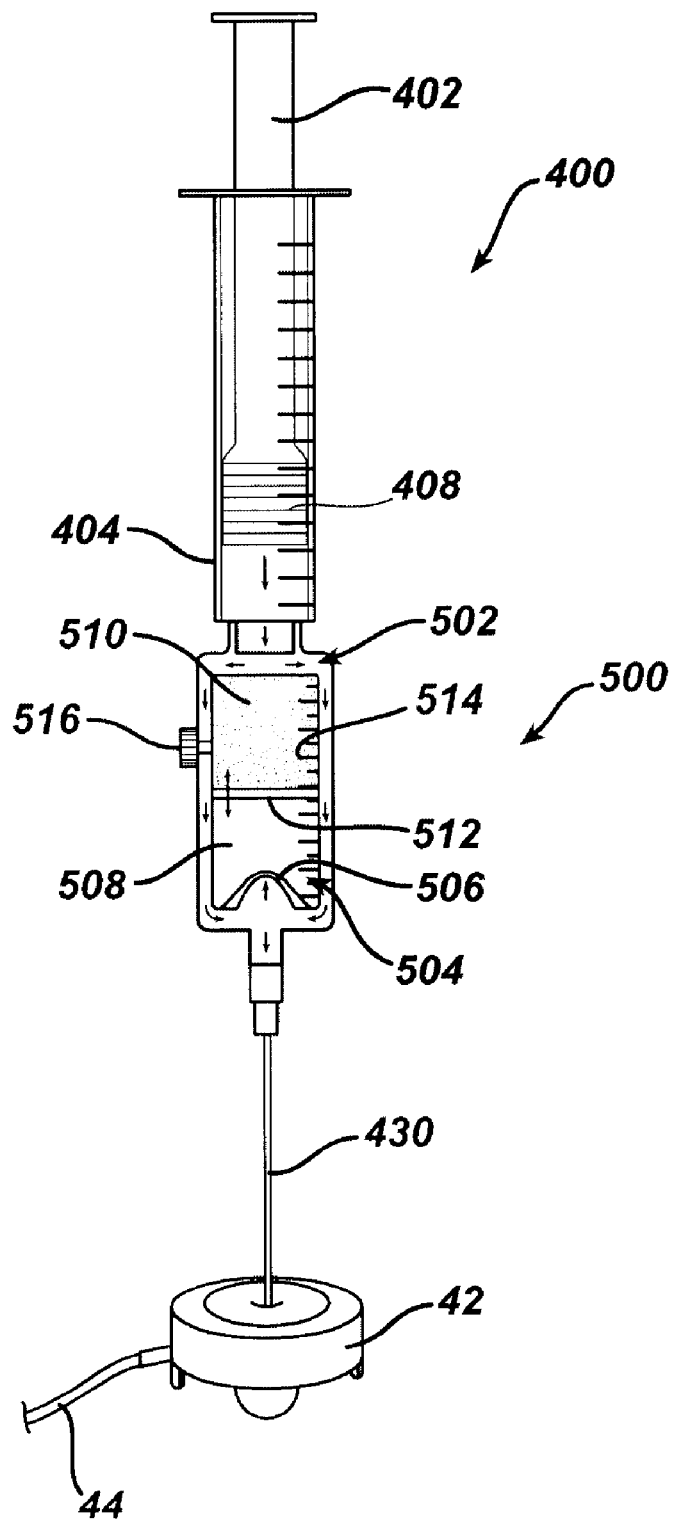
FIG. 15 is a cross-sectional view of an alternative exemplary pressure sensing syringe system including a directly in-line pressure sensor.

FIG. 15 shows a syringe 400 coupled with a pressure sensing component 500. Syringe 400 is a conventional syringe, and comprises a plunger 402, barrel 404, piston 408, and needle 430 like syringe 400 of FIGS. 6 and 10. Pressure sensing component 500 is selectively connectable with barrel 404 and needle 430 of syringe 400. For instance, such selective connectivity may be provided by complimentary luer lock features or by other structures. Pressure sensing component 500 comprises a fluid flow chamber 502 and a pressure reading chamber 504. In the present example, pressure sensing component 500 is configured such that fluid may be communicated from barrel 404 to needle 430 via fluid flow chamber 502 when pressure sensing component 500 is coupled with barrel 404 and needle 430.

In this example, fluid flow chamber 502 and pressure reading chamber 504 are not in fluid communication. However, as will be described in greater detail below, a portion of fluid flow chamber 502 and a portion of pressure reading chamber 504 are separated by a diaphragm 506. Pressure reading chamber 504 comprises a first medium 508 and a second medium 510, which are separated by an indicator 512. Indicator 512 of the present example comprises a plastic disc, though any other suitable structures or materials may be used. Furthermore, while indicator 512 of the present example comprises a disc, it will be appreciated that such a disc or any other indicator 512 may have any other suitable shape or configuration, and it need not necessarily be round. In the present example, first medium 508 and second medium 510 comprise different materials, though first medium 508 and second medium 510 may alternatively comprise the same material. First medium 508 and/or second medium 510 may be selected from the following group: any fluid (e.g., gas, liquid), gel, foam, one or more springs, including combinations thereof. Other suitable materials and structures for first medium 508 and second medium 510 will be apparent to those of ordinary skill in the art. It will also be appreciated that certain selections of materials for first medium 508 and second medium 510 may obviate the need for a separate indicator 512, as an interface of first medium 508 and second medium 510 may serve a function similar to indicator 512 as described below.

Indicator 512 is configured to move up and down within pressure reading chamber 504 in response to pressure variations communicated via diaphragm 506. In particular, diaphragm 506 is configured such that pressure of fluid within fluid flow chamber 502 will cause a corresponding deformation of diaphragm 506. Such deformation of diaphragm 506 will be communicated through first medium 508, which will cause a corresponding rise or fall of indicator 512 within pressure reading chamber 504.

Pressure reading chamber 504 of the present example further comprises a plurality of graduations 514. It will be appreciated that the position of indicator 512 relative to graduations 514 may provide a visual indication of fluid pressure within fluid flow chamber 502. It will also be appreciated that, to the extent that the pressure of fluid within implanted portion 32 is substantially equalized with the pressure of fluid within fluid flow chamber 502 (e.g., when needle 430 has been inserted into port 42), indicator 512 and graduations 514 may provide an indication of the fluid pressure within implanted portion 32. Accordingly, a syringe 400 coupled with a pressure sensing component 500 may be used in a manner similar to that described above with respect to the embodiments depicted in FIGS. 6-13, albeit relying on mechanical-based pressure measurements rather than electronic-based pressure measurements. In other words, in some versions of this embodiment and versions of other embodiments described herein, the pressure of fluid may be sensed and measured with a pressure sensing component 500 substantially contemporaneously with an act of adjusting fluid pressure with a syringe 400.

As shown, pressure sensing component 500 further comprises a capped vent 516 in communication with pressure reading chamber 504. Pressure sensing component 500 may therefore be used to obtain measurements of gauge pressure. The structure of capped vent 516, alone or in combination with other features not depicted, may also secure pressure reading chamber 504 relative to fluid flow chamber 502. In an alternate embodiment, capped vent 516 is eliminated, such that pressure sensing component 500 may be used to obtain measurements of absolute pressure. Such embodiments, among others, may rely on any suitable structures to secure pressure reading chamber 504 relative to fluid flow chamber 502. Still other suitable variations of pressure sensing component 500 will be apparent to those of ordinary skill in the art, as the embodiments explicitly described herein are not intended to be exhaustive.

As shown in FIG. 15, pressure sensing component 500 is directly "in line" with the other components of syringe 400. In other words, a straight line is able to intersect pressure sensing component 500 and other components of syringe 400. Of course, pressure sensing component 500 need not be directly in line with syringe 400 per se. For instance, pressure sensing component 500 may be merely substantially in line with syringe 400 as described above with respect to the embodiment depicted in FIG. 6. Alternatively, any other suitable relationship between pressure sensing component 500 and syringe 400 may be used.

Figure 16:
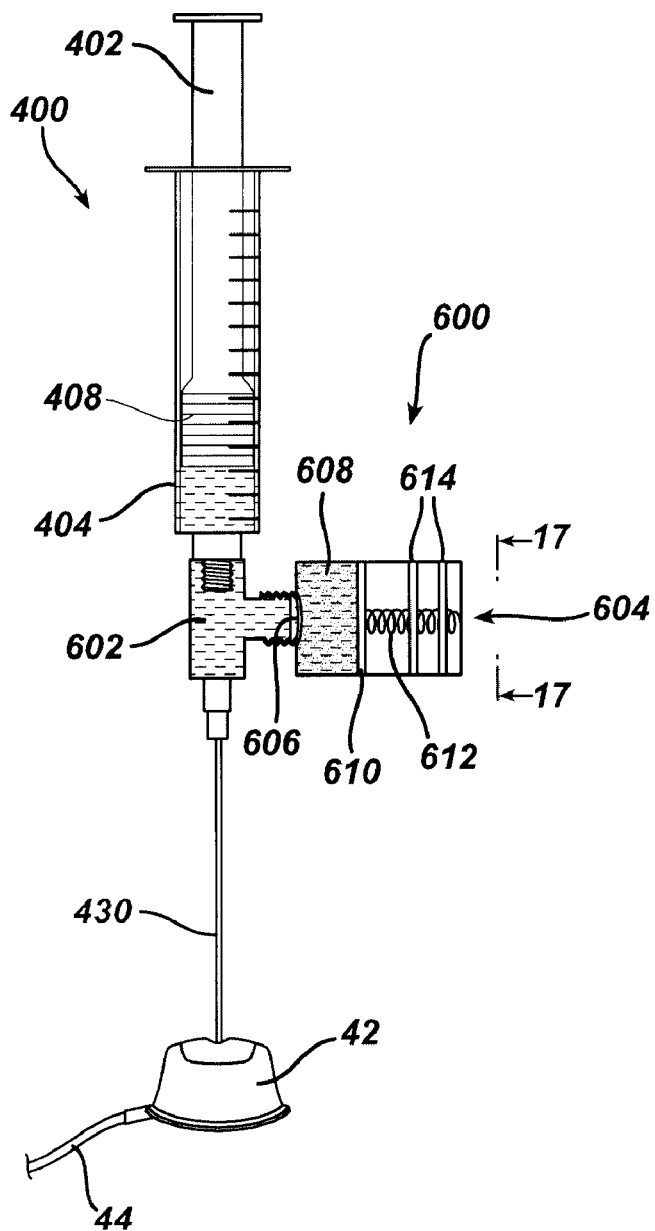
FIG. 16 is a cross-sectional view of an alternative exemplary pressure sensing syringe system including a piston-based pressure sensor.
Figure 17:
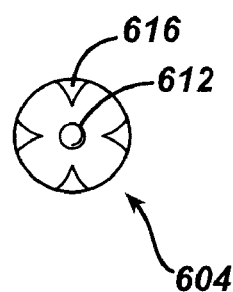
FIG. 17 is a cross-sectional view of the pressure sensor of FIG. 16, taken along line 17-17.

Another mechanical-based pressure measurement system is shown in FIGS. 16-17. In this embodiment, a conventional syringe 400 is coupled with a pressure sensing component 600. Pressure sensing component 600 of this example comprises a "T"-shaped fitting 602 and a pressure sensor 604. "T"-shaped fitting 602 is selectively coupled with barrel 404 of syringe 400, needle 430 of syringe 400, and pressure sensor 604. As with other embodiments described herein, such selective coupling may be provided by complimentary luer lock features or other structures. Alternatively, any components described herein as selectively connectable may be integral or otherwise fixedly and permanently secured to one another. In any event, "T"-shaped fitting 602 of the present example is in fluid communication with the components to which it is coupled, and is configured to permit fluid communication from barrel 404 to needle 430. Of course, the "T" shape of "T"-shaped fitting 602 is merely exemplary. Those of ordinary skill in the art will immediately recognize that any fitting described herein may have any suitable alternative shape (e.g., "Y" shape).

In one embodiment, the interface of barrel 404 and "T"-shaped fitting 602 comprises a luer activated valve (not shown) or other feature configured to selectively prevent communication of fluid at the interface. For instance, a luer activated valve may be provided on the barrel 404 side of the interface and configured to block communication of fluid into and/or out of barrel 404 at the interface until barrel 404 is coupled with "T"-shaped fitting 602. In addition or in the alternative, a luer activated valve may be provided on the "T"-shaped fitting 602 side of the interface and configured to block communication of fluid into and/or out of "T"-shaped fitting 602 at the interface until "T"-shaped fitting 602 is coupled with barrel 404. As will be appreciated in view of the teachings herein, such a luer activated valve may prevent backflow, address hysteretic effects, reduce the likelihood of plunger 402 movement while pressure is sensed, provide other results, or provide no appreciable results. Furthermore, a luer activated valve may be provided on either side or both sides of any other interface described herein. For instance, a luer activated valve may be provided at either or both sides of interface of "T"-shaped fitting 602 and pressure sensor 604; or at interface of "T"-shaped fitting 602 and needle 430. It will also be appreciated that any other device or structure may be provided at or near either or both sides of any interface described herein, including but not limited to a one-way valve, a stopcock, or any other device or structure to provide similar or different results. Alternatively, such devices or structures may be omitted altogether.

Pressure sensor 604 of the present example comprises a diaphragm 606, a medium 608, a piston 610, a pressure-calibrated spring 612, markings 614, and vent holes 616. Medium 608 may comprise any suitable material including but not limited to gel, air, any other gas, or any liquid. Similar to diaphragm 506 of FIG. 15, diaphragm 606 of FIG. 16 is configured to deform in response to fluid pressure within "T"-shaped fitting 602. Such deformation of diaphragm 606 may be communicated through medium 608 to piston 610. Piston 610 may therefore move within pressure sensor 604 in response to changes of pressure within "T"-shaped fitting 602. Vent holes 616 formed in pressure sensor 604 may permit movement of air into and out of pressure sensor 604 as piston 610 moves.

Pressure-calibrated spring 612 is coupled or engaged with piston 610, and is configured to resist movement of piston 610. Suitable properties (e.g., spring constant, material, etc.) for pressure-calibrated spring 612 will be apparent to those of ordinary skill in the art. Markings 614 are provided to indicate optimal pressure values or ranges. In other words, the position of piston 610 relative to markings 614 may be viewed for indication of fluid pressure within "T"-shaped fitting 602. As will be apparent to those of ordinary skill in the art, the pressure of fluid within "T"-shaped fitting 602 may be indicative of the pressure of fluid within implanted portion 32. Suitable methods for determining optimal pressure values or ranges, and therefore locations for markings 614 on pressure sensor 604, will also be apparent to those of ordinary skill in the art.

Figure 18:
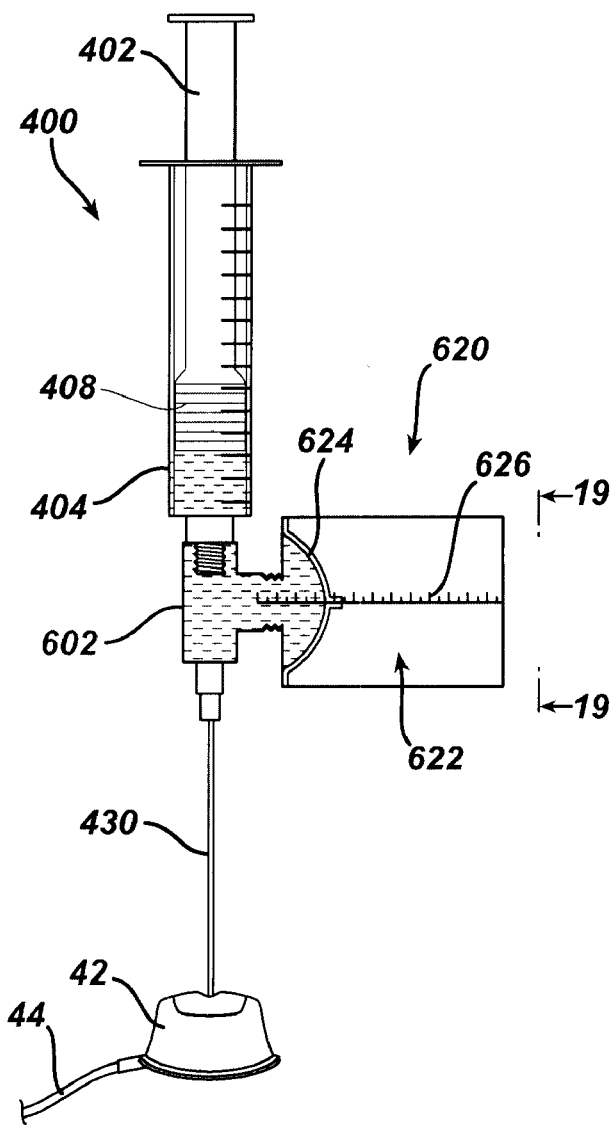
FIG. 18 is a cross-sectional view of an alternative exemplary pressure sensing syringe system including a diaphragm-based pressure sensor.
Figure 19:
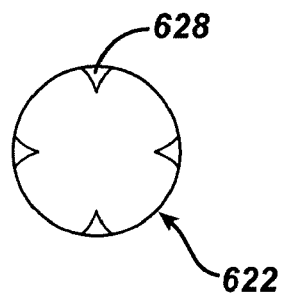
FIG. 19 a cross-sectional view of the pressure sensor of FIG. 16, taken along line 19-19.

FIGS. 18-19 show yet another mechanical-based pressure measurement system. In this embodiment, a conventional syringe 400 is coupled with a pressure sensing component 620. Pressure sensing component 620 of this example comprises a "T"-shaped fitting 602 and a pressure sensor 622. The relationship between "T"-shaped fitting 602 and syringe 400 components in this embodiment, and the relationship between "T"-shaped fitting 602 and pressure sensor 622 in this embodiment, are essentially the same as those relationships described above with respect to the embodiment depicted in FIGS. 16-17.

Pressure sensor 622 of the present example comprises a pressure-calibrated diaphragm 624, graduations 626, and vent holes 628. As with other diaphragms 506, 606 described herein, pressure-calibrated diaphragm 624 is configured to deform in response to fluid pressure within "T"-shaped fitting 602. Vent holes 628 formed in pressure sensor 622 may permit movement of air into and out of pressure sensor 622 as pressure-calibrated diaphragm 624 deforms. Graduations 626 are provided along pressure sensor 622 to indicate fluid pressure measurements. In particular, the position of pressure-calibrated diaphragm 624 relative to graduations 626 may be viewed for measurement of fluid pressure within "T"-shaped fitting 602. As noted above, the pressure of fluid within "T"-shaped fitting 602 may be indicative of the pressure of fluid within implanted portion 32.

Figure 20:
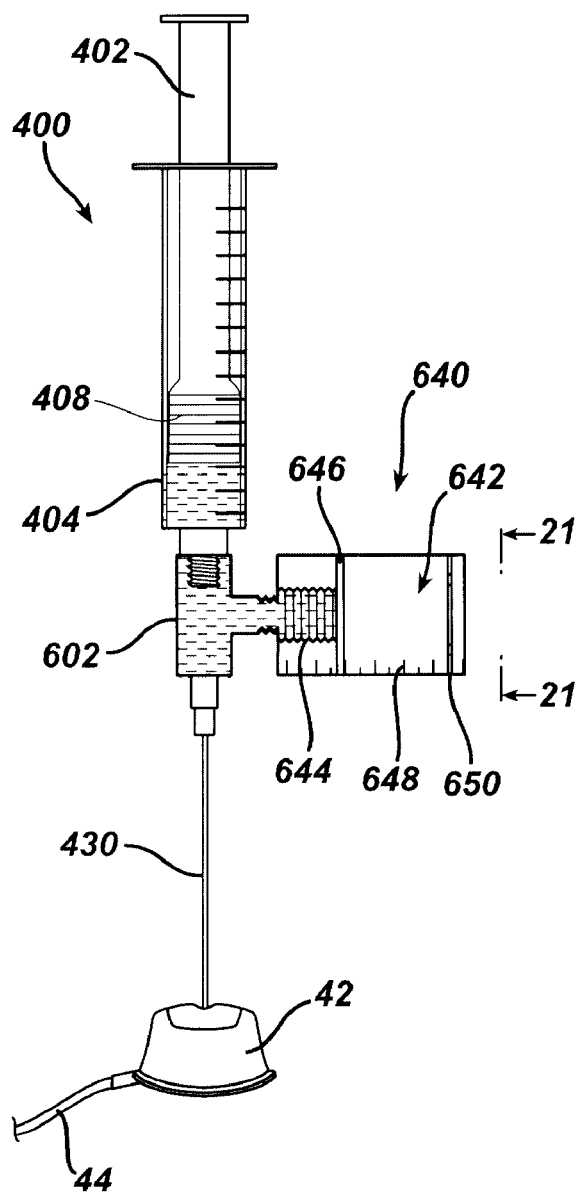
FIG. 20 is a cross-sectional view of an alternative exemplary pressure sensing syringe system including a bellows-based pressure sensor.
Figure 21:
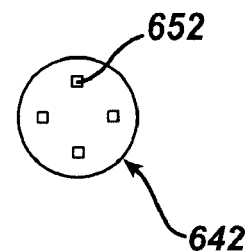
FIG. 21 is a cross-sectional view of the pressure sensor of FIG. 16, taken along line 21-21.

Still another mechanical-based pressure measurement system is shown in FIGS. 20-21. In this embodiment, a conventional syringe 400 is coupled with a pressure sensing component 640. Pressure sensing component 640 of this example comprises a "T"-shaped fitting 602 and a pressure sensor 642. The relationship between "T"-shaped fitting 602 and syringe 400 components in this embodiment, and the relationship between "T"-shaped fitting 602 and pressure sensor 642 in this embodiment, are essentially the same as those relationships described above with respect to the embodiments depicted in FIGS. 16-19.

Pressure sensor 642 of the present example comprises a pressure-calibrated bellows 644, a piston 646, graduations 648, a threshold marking 650, and vent holes 652. Bellows 644 and piston 646 are coupled together, and bellows 644 and piston 646 are configured to move within pressure sensor 642. The interior of bellows 644 is in fluid communication with "T"-shaped fitting 602. In this embodiment, the combination of bellows 644 and piston 646 operate in a manner similar to that of diaphragm 624 in the embodiment depicted in FIG. 18. That is, bellows 644 and piston 646 are configured to move within pressure sensor 642 in response to changes of fluid pressure within "T"-shaped fitting 602. Vent holes 652 formed in pressure sensor 642 may permit movement of air into and out of pressure sensor 642 as bellows 644 and piston 646 move within pressure sensor 642.

Graduations 648 are provided along pressure sensor 642 to indicate fluid pressure measurements. In particular, the position of piston 646 relative to graduations 648 may be viewed for measurement of fluid pressure within "T"-shaped fitting 602. As noted above, the pressure of fluid within "T"-shaped fitting 602 may be indicative of the pressure of fluid within implanted portion 32. Furthermore, threshold marking 650 within pressure sensor 642 provides an indication of the maximum amount of fluid pressure that should be provided. In other words, as the position of piston 646 approaches the threshold marking 650, a user may be so notified that additional fluid should not be injected with syringe 400 lest the fluid pressure threshold be exceeded. Suitable methods for determining a maximum pressure threshold will be apparent to those of ordinary skill in the art, and may be based on properties of implanted portion 32, patient 34 parameters, and/or other considerations. It will also be appreciated that a threshold marking 650 may be provided in or with any other pressure sensor described herein.

Figure 22:
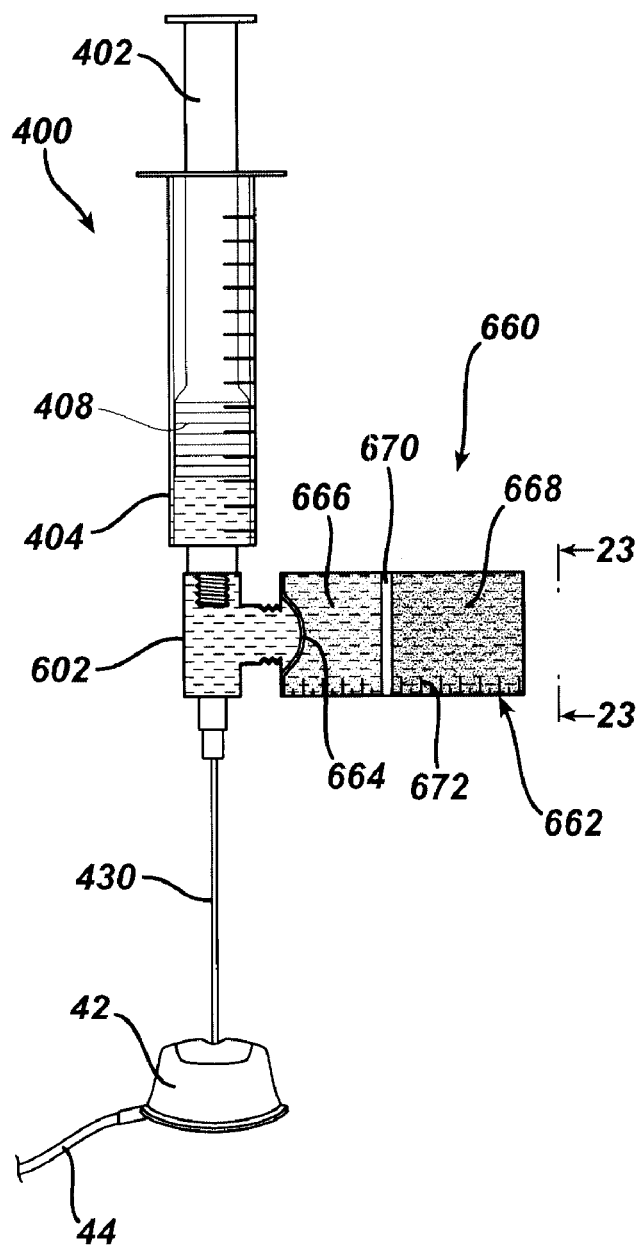
FIG. 22 is a cross-sectional view of an alternative exemplary pressure sensing syringe system including a pressure sensor using a plurality of media.
Figure 23:
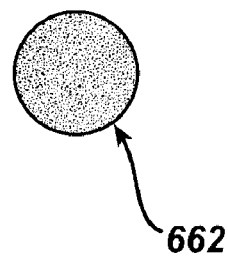
FIG. 23 is a cross-sectional view of the pressure sensor of FIG. 16, taken along line 23-23.

FIGS. 22-23 show yet another exemplary mechanical-based pressure measurement system. In this embodiment, a conventional syringe 400 is coupled with a pressure sensing component 660. Pressure sensing component 660 of this example comprises a "T"-shaped fitting 602 and a pressure sensor 662. The relationship between "T"-shaped fitting 602 and syringe 400 components in this embodiment, and the relationship between "T"-shaped fitting 602 and pressure sensor 662 in this embodiment, are essentially the same as those relationships described above with respect to the embodiments depicted in FIGS. 16-21.

Pressure sensor 662 of the present example comprises a diaphragm 664, a first medium 666, a second medium 668, an indicator 670, and graduations 672. Indicator 670 separates first medium 666 from second medium 668. Indicator 670 of the present example comprises a plastic disc, though any other suitable structures or materials may be used. In the present example, first medium 666 and second medium 668 comprise different materials, though first medium 666 and second medium 668 may alternatively comprise the same material. First medium 666 and/or second medium 668 may be selected from the following group: any fluid (e.g., gas, liquid), gel, foam, one or more springs, including combinations thereof. Other suitable materials and structures for first medium 666 and second medium 668 will be apparent to those of ordinary skill in the art. It will also be appreciated that certain selections of materials for first medium 666 and second medium 668 may obviate the need for a separate indicator 670, as an interface of first medium 666 and second medium 668 provide a functional equivalent of indicator 670 as described below.

Indicator 670 is configured to move within pressure sensor 662 in response to pressure variations communicated via diaphragm 664. In particular, diaphragm 664 is configured such that pressure of fluid within "T"-shaped fitting 602 will cause a corresponding deformation of diaphragm 664. Such deformation of diaphragm 664 will be communicated through first medium 666, which will cause a corresponding movement of indicator 670 within pressure sensor 662. Of course, as with any other diaphragm described herein, diaphragm 664 may be substituted with any suitable structure, including but not limited to a bellows.

Pressure sensor 662 of the present example further comprises a plurality of graduations 672. It will be appreciated that the position of indicator 670 relative to graduations 672 may provide an indication of fluid pressure within "T"-shaped fitting 602. It will also be appreciated that, to the extent that the pressure of fluid within implanted portion 32 is substantially equalized with the pressure of fluid within "T"-shaped fitting 602 (e.g., when needle 430 has been inserted into port 42), indicator 670 and graduations 672 may provide an indication of the fluid pressure within implanted portion 32. Accordingly, the embodiment depicted in FIGS. 22-23 operates in a manner similar to the manner in which the embodiment depicted in FIG. 15 operates. However, the pressure sensor 662 of FIGS. 22-23 is not directly in line with syringe 400.

Figure 24:
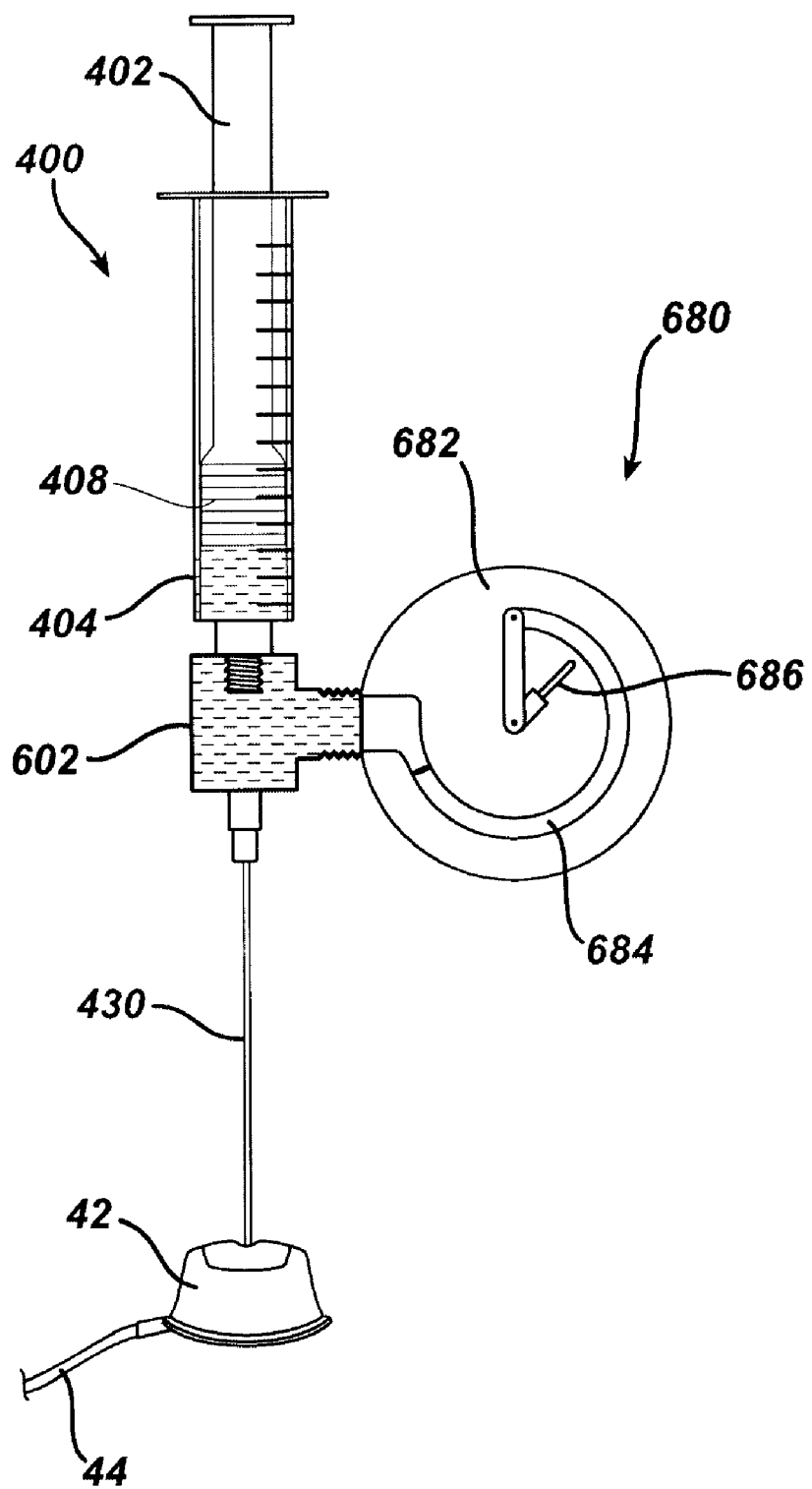
FIG. 24 is a cross-sectional view of an alternative exemplary pressure sensing syringe system including a pressure sensor using a Bourdon tube pressure gauge.

Another exemplary mechanical-based pressure measurement system is depicted in FIG. 24. In this embodiment, a conventional syringe 400 is coupled with a pressure sensing component 680. Pressure sensing component 680 of this example comprises a "T"-shaped fitting 602 and a Bourdon tube pressure gauge 682. The relationship between "T"-shaped fitting 602 and syringe 400 components in this embodiment, and the relationship between "T"-shaped fitting 602 and Bourdon tube pressure gauge 682 in this embodiment, are essentially the same as those relationships described above with respect to the embodiments depicted in FIGS. 16-23.

Bourdon tube pressure gauge 682 of this example comprises a conventional Bourdon tube pressure gauge assembly. In particular, Bourdon tube pressure gauge 682 comprises a Bourdon tube 684 and an indicator needle 686. Bourdon tube pressure gauge 682 is configured such that needle 686 moves in response to changes in fluid pressure within "T"-shaped fitting 602. While not depicted in FIG. 24, needle 686 may be presented in front of a face having pressure indications marked thereon, such that pressure measurements may be obtained by viewing the position of needle 686 relative to such markings. As noted above, measurements of the pressure of fluid within "T"-shaped fitting 602 may be indicative of the pressure of fluid within implanted portion 32.

Figure 25:
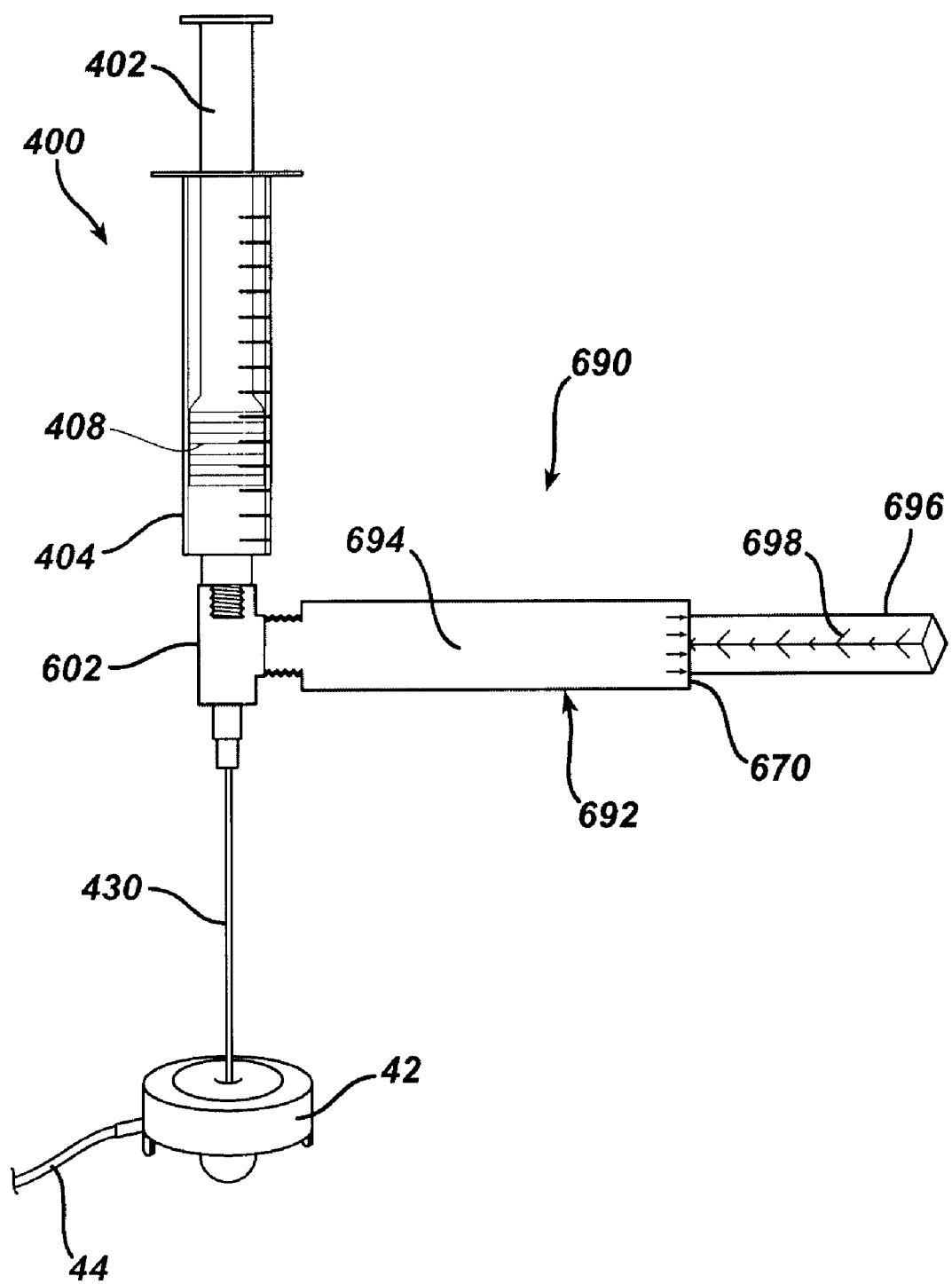
FIG. 25 is a plan view of an alternative exemplary pressure sensing syringe system including a pressure sensor using a slide gauge.

FIG. 25 shows yet another exemplary mechanical-based pressure measurement system. In this embodiment, a conventional syringe 400 is coupled with a pressure sensing component 690. Pressure sensing component 690 of this example comprises a "T"-shaped fitting 602 and a slide gauge 692. The relationship between "T"-shaped fitting 602 and syringe 400 components in this embodiment, and the relationship between "T"-shaped fitting 602 and slide gauge 692 in this embodiment, are essentially the same as those relationships described above with respect to the embodiments depicted in FIGS. 16-24.

Slide gauge 692 of this example is similar to conventional slide gauges that are often used to measure the pressure of air in tires. In particular, slide gauge comprises an elongate housing 694 and a slider 696 that is configured to move longitudinally into and out of housing 694. That is, slider 696 moves in response to changes in fluid pressure within "T"-shaped fitting 602. A seal is provided between slider 696 and housing 694 to prevent leakage of fluid therebetween. A plurality of graduations 698 are provided on slider 696 to indicate pressure measurements, such that pressure measurements may be obtained by viewing the position of graduations 698 relative to the end 670 of housing 694. As noted above, measurements of the pressure of fluid within "T"-shaped fitting 602 may be indicative of the pressure of fluid within implanted portion 32.

To the extent that any of the foregoing embodiments include leur-type interfaces (e.g., ports of "T"-shaped fittings 602, etc.), it will be appreciated that such interfaces may comprise conventional luer lock structures. It will also be appreciated that such interfaces may comprise a luer-activated valve or other feature. Furthermore, any pressure sensor described herein may be configured to measure absolute pressure or gauge pressure. Still further, while pressure sensors are described herein as being coupled with conventional syringe components, it will be appreciated that any of the pressure sensors described herein may alternatively be integral with a plunger 402, a barrel 404, a needle 430, or any other component.

While several exemplary mechanical-based pressure sensing systems and components have been discussed above, it will be appreciated that the embodiments explicitly described are not intended to be exhaustive. Various components described above may be varied, substituted, supplemented, moved, rearranged from one embodiment to another, merged, combined, and/or separated. Suitable modifications will be apparent to those of ordinary skill in the art.

In addition to use during adjustments, the pressure sensing systems of the foregoing examples may also be used to measure pressure variations in implanted portion 32 at various intervals during treatment. Periodic pressure readings may enable the pressure sensing system to function as a diagnostic tool, to ensure that adjustable band 38 is operating effectively. In particular, a pressure sensing system may be utilized to detect a no pressure condition within band 38, which may indicate a fluid leakage or other condition. Alternatively, the system may be used to detect excessive pressure spikes within band 38, which may indicate a kink in catheter 44 or a blockage within the stoma or other conditions.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

The present invention has application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to providing the pressure sensor within the injection port. Alternatively, the sensor could be positioned within a fluid filled portion of the band in order to measure pressure changes within the band. Additionally, the pressure sensor could be associated with an elastomeric balloon implanted within the stomach cavity to measure fluid pressure within the balloon. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. An external pressure sensing system, the system comprising:
   (a) a connecting member operable to connect to a syringe barrel, wherein the connecting member is further operable to connect to a needle, wherein the connecting member comprises a conduit permitting communication of fluid from the syringe barrel to the needle when the connecting member is connected to the syringe barrel and the needle, wherein at least a portion of the connecting member is positioned to maintain coaxial alignment in relation to the needle, wherein the at least a portion of the connecting member is positioned to maintain coaxial alignment in relation to the syringe barrel, wherein the connecting member is configured to maintain a distance between the syringe barrel and the needle such that the syringe barrel and the needle is configured for single-handed use; and
   (b) a pressure sensor in communication with the conduit, wherein the pressure sensor comprises an outer body, wherein the pressure sensor is configured to sense pressure of fluid within the connecting member, wherein the connecting member is configured to permit the pressure sensor to sense the pressure of the fluid while the fluid is communicated from the barrel to the needle, wherein the pressure sensor is configured to provide a visual indication of sensed pressure, wherein the visual indication of the sensed pressure is confined within a volume defined by the outer body of the pressure sensor.

2. The external pressure sensing system of claim 1, wherein the pressure sensor comprises a movable indicator, wherein the movable indicator is configured to move in response to changes in pressure of the fluid.

3. The external pressure sensing system of claim 2, wherein the pressure sensor comprises a first medium and a second medium, wherein the first medium and the second medium are separated by the movable indicator.

4. The external pressure sensing system of claim 2, wherein the movable indicator is positioned such that the movable indicator is intersected by an axis defined by a syringe barrel and a needle when the connecting member is connected to the syringe barrel and the needle.

5. The external pressure sensing system of claim 2, wherein the movable indicator is engaged with a resilient member.

6. The external pressure sensing system of claim 5, wherein the resilient member comprises one or both of a spring or a bellows.

7. The external pressure sensing system of claim 2, wherein the movable indicator comprises one or more of a diaphragm, a disc, a needle, or a slider.

8. The external pressure sensing system of claim 1, wherein the pressure sensor is free of electronic components.

9. The external pressure sensing system of claim 1, wherein the pressure sensor is housed within the connecting member.

10. The external pressure sensing system of claim 9, wherein the connecting member has a first connection port, a second connection port, and a third connection port.

11. The external pressure sensing system of claim 10, wherein the first connection port is configured to engage with a syringe barrel, wherein the second connection port is configured to engage with a syringe needle, and wherein the third connection port is configured to engage with the pressure sensor.

12. The external pressure sensing system of claim 1, wherein the pressure sensor comprises a member marked with graduations indicative of pressure levels.

13. An external pressure sensing kit for use with a gastric band system comprising a fluid-fillable band, the kit comprising:
   (a) a syringe, wherein the syringe comprises:
      (i) a barrel,
      (ii) a plunger, wherein at least a portion of the plunger is configured to fit within the barrel, and
      (iii) a needle,
      wherein the syringe is configured to be in selective fluid communication with the gastric band system, wherein the syringe is operable to adjust an amount of fluid contained in the gastric band system, wherein the fluid-filled band of the gastric band system is configured to form a gastric restriction within a patient; and
   (b) a pressure sensing system, wherein the pressure sensing system comprises:
      (i) a connector, wherein the connector is configured to fit between the barrel and the needle, wherein the connector provides a fluid path configured to permit communication of fluid from the barrel to the needle,
      (ii) a pressure sensor in communication with the connector, wherein the pressure sensor is configured to sense pressure of fluid within the connector as fluid moves from the barrel to the needle or from the needle to the barrel when the connector is attachably positioned between the barrel and the needle such that the syringe and the pressure sensing system are together structurally sized and configured to be operable using a single-handed operation, wherein the pressure sensor is configured to provide a visual indication of sensed pressure.

14. The external pressure sensing kit of claim 13, wherein the pressure sensor comprises a housing externally attached to the connector.

15. The external pressure sensing kit of claim 13, wherein the pressure sensor is housed within the connector.

16. The external pressure sensing kit of claim 13, wherein the pressure sensor comprises a pressure indicator, wherein the pressure indicator is operable to move in response to changes in pressure within the connector.

17. The external pressure sensing kit of claim 16, wherein the pressure indicator comprises one or more of a disc, a diaphragm, a needle, or a slider.

18. A method for externally measuring the pressure of fluid in a gastric band system using a syringe assembly and an external pressure sensor assembly in fluid communication with the syringe assembly, wherein the gastric band system comprises an injection port and a fluid-filled band in fluid communication with the injection port, wherein the syringe assembly comprises a syringe barrel and a needle, wherein the syringe barrel comprises a fluid, wherein the needle is in fluid communication with the barrel, wherein the external pressure sensor assembly is locatable external to a patient, wherein the external pressure assembly comprises a movable indicator configured to indicate sensed pressure, the method comprising:

(a) inserting the needle of the syringe assembly into the patient, wherein the needle is inserted into the injection port of the gastric band system, which is located within the patient, wherein the fluid injection port comprises a fluid;

(b) establishing fluid communication between the syringe assembly and the fluid-filled band of the gastric band system via the injection port;

(c) adjusting the pressure of fluid in the gastric band system, wherein the act of adjusting comprises manipulating the syringe assembly to add fluid to the port or to withdraw fluid from the port; and (d) obtaining a pressure reading with the external pressure sensor assembly while adjusting the pressure of fluid in the gastric band system, wherein the pressure data relates to the pressure of the fluid within at least a portion of the syringe assembly, wherein the act of obtaining a pressure reading comprises viewing the movable indicator.

19. The method of claim 18, wherein the act of obtaining a pressure reading and the act of adjusting the pressure of fluid in the injection port are performed substantially simultaneously.

20. The method of claim 18, wherein the external pressure sensor assembly is free of electronic components.

* * * * *